United States Patent [19]

Shanklin, Jr. et al.

[11] Patent Number: 4,835,164
[45] Date of Patent: May 30, 1989

[54] ARYLOXYMETHYL DERIVATIVES OF NITROGENOUS HETEROCYCLIC METHANOLS AND ETHERS THEREOF

[75] Inventors: James R. Shanklin, Jr.; Christopher P. Johnson, III, both of Richmond, Va.

[73] Assignee: A. H. Robins Company, Incorporated, Richmond, Va.

[21] Appl. No.: 16,779

[22] Filed: Feb. 20, 1987

[51] Int. Cl.$^4$ .................. A61K 31/445; A61K 31/40; A61K 31/55; C07D 211/22

[52] U.S. Cl. .................................. 514/317; 514/211; 514/212; 514/230.5; 514/319; 514/321; 514/331; 514/422; 514/428; 540/579; 540/596; 540/609; 544/105; 546/197; 546/205; 546/232; 546/236; 546/240; 548/526; 548/570

[58] Field of Search ............... 540/596, 609; 546/197, 546/205, 232, 236, 240; 548/526, 570; 514/212, 317, 319, 321, 331, 422, 428

[56] References Cited

FOREIGN PATENT DOCUMENTS 2521136 8/1983 France .

OTHER PUBLICATIONS

Winterfeld et al., Chemical Abstracts, vol. 53 (1959) 18032 c.

Primary Examiner—Richard L. Raymond

[57] ABSTRACT

Novel heterocyclicmethanols are disclosed having the formula:

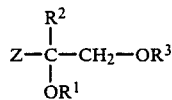

wherein Z is pyrrolidinyl, piperidinyl, homopiperidinyl or pyridinyl;
 $R^1$ is hydrogen, loweralkyl or carbethoxymethyl;
 $R^2$ is hydrogen, loweralkyl, cycloalkyl, phenyl or phenyl-loweralkyl;
 $R^3$ is 1 or 2-naphthalenyl, 2,3-dihydroinden-4 or 5-yl, phenyl or phenyl substituted by loweralkyl, loweralkoxy, halogen, trifluoromethyl, phenyl, methylenedioxy, nitro, amino, loweralkylamino, diloweralkylamino, loweracylamino;
 the 1-position of 2-pyrrolidinyl, 2-piperidinyl or 2-homopiperidinyl may be substituted by an $R^4$ loweralkyl group, or $R^1$ may form methylene or —$CH_2$-C(O)-bridges with $R^4$;
 the pharmaceutically acceptable salts and diastereomers thereof, which compounds have antiarrhythmic and/or hypotensive activity in animals.

45 Claims, No Drawings

ARYLOXYMETHYL DERIVATIVES OF NITROGENOUS HETEROCYCLIC METHANOLS AND ETHERS THEREOF

BACKGROUND OF THE INVENTION

1. Field of the Invention

The present invention relates to novel derivatives of nitrogen-containing heterocyclic methanols, encompassing derivatives of pyrrolidine, piperidine, homopiperidine and pyridine methanols, having α-aryloxymethyl substitution and certain double ethers thereof. The compounds are useful in treating cardiac related conditions in animals.

2. Information Disclosure Statement

Various related compounds are known in the art. For example, compounds of the formula:

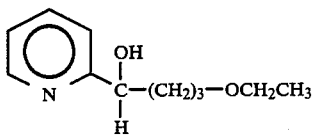

are known, *J. Org. Chem.* 23, p. 435 (1958). Compounds of the formula:

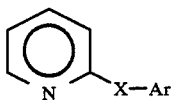

are known where X=O-alkyl, alkyl-O, or alkyl-O-alkyl as described in British Pat. No. 1,437,781. Compounds of the formula:

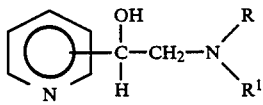

ps are also known. *Farmaco, Ed. Sci.,* 18(12), pp. 972-80 (1963); *J. Med. Chem.* 16(9), p. 1040 (1973); *J. Med. Chem.* 15(12), p. 1321 (1972).

SUMMARY OF THE INVENTION

The novel aryloxymethyl derivatives of heterocyclic methanols of this invention have the formula:

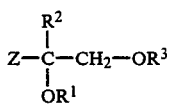

Formula I wherein Z is selected from the group consisting of

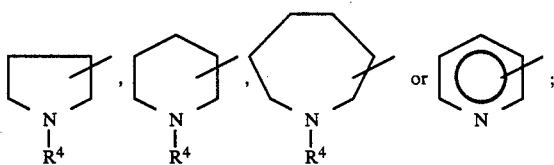

$R^1$ is selected from hydrogen, loweralkyl or carbethoxymethyl;

$R^2$ is selected from hydrogen, loweralkyl, cycloalkyl, phenyl, or phenyl-loweralkyl;

$R^3$ is an aryl group selected from 1 and 2-naphthalenyl, 2,3-dihydroinden-4-yl, 2,3-dihydroinden-5-yl, phenyl or phenyl substituted by one to three radicals selected from
loweralkyl,
loweralkoxy,
halogen,
trifluoromethyl,
phenyl,
methylenedioxy,
nitro,
amino,
loweralkylamino,
diloweralkylamino,
loweracylamino;

$R^4$ is hydrogen or loweralkyl;

$R^1$ and $R^4$ when taken together may form a dimethylene bridge or a —CH$_2$C(O)-bridge, the side chain bearing aryloxymethyl group being linked to the 2-position of pyrrolidine, piperidine or homopiperidine moiety; and the pharmaceutically acceptable acid addition salts thereof and the diastereomers thereof.

In the further definition of symbols in the formulas hereof and where they appear elsewhere throughout this specification and the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert.-butyl, amyl, isoamyl, hexyl, heptyl and octyl radicals and the like. The term "loweralkoxy" has the formula —O-loweralkyl.

The term "cycloalkyl" as used herein includes primarily cyclic alkyl radicals containing 3–9 carbon atoms inclusive and includes such groups as cyclopropyl, cyclobutyl, cyclopentyl, cyclohexyl, methylcyclohexyl, cycloheptyl and the like. The terms "halo" or "halogen" when referred to herein include fluorine, chlorine, bromine and iodine unless otherwise stated.

Phenyl in the definition of $R^2$ may include common 1-3 non-interfering radicals exemplified by halo, loweralkyl, loweralkoxy, nitro, trifluoromethyl and the like.

By "double ether" is meant a compound having an "—O-loweralkyl" group in addition to the aryloxy group represented by "—OR$^3$" in Formula I.

"Pharmaceutically acceptable salts" include acid addition salts and hydrates of the compounds of Formula I which are physiologically compatible in warm blooded animals. The acid addition salts may be formed by either strong or weak acids. Representative of strong acids are hydrochloric, sulfuric and phosphoric acids. Representative of weak acids are fumaric, maleic, succinic, oxalic, citric, tartaric, hexamic and the like.

By the term "loweracylamino" is meant

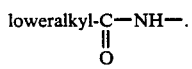

The compounds of the present invention act to correct ouabain-induced cardiac arrhythmias and/or lower blood pressure in hypertensive living animals as described more fully hereinbelow under "Pharmacology."

The method of treating cardiac arrhythmias and hypertension in living animals comprises administering compounds of Formula I to a living animal body for cardiac arrhythmic effect and/or blood pressure-lowering effect in an effective amount to control arrhythmia and/or blood pressure as set forth hereinbelow under "Pharmaceutical Compositions and Administration."

It is therefore an object to provide novel aryloxymethyl derivatives of nitrogenous heterocyclic methanols having antiarrhythmic and hypotensive properties in living animals, methods of treatment therewith, and pharmaceutical compositions thereof.

Additional objects will become apparent to one skilled in the art and still others will become apparent hereinafter.

Methods of preparing pyridine and piperidine derivatives of Formula I are diagrammed in Chart I. The starting acetyl pyridine compounds are available commercially.

Methods of preparing pyrrolidine, piperidine and homopiperidine compounds of Formula I are diagrammed in Chart II. Starting materials are the carboxylic acids or the hydroxymethyl derivatives, sources of which are given in the footnotes. An alternate method of preparing the 2-aryloxymethyl-pyrrolidinyl, piperidinyl and homopiperidinyl compounds of Formula I is given in Chart III, the starting materials being pyrrolidine and piperidine, available commercially and homopiperidine which can be readily prepared by known methods. Ethers ($R^1$ = loweralkyl) are prepared as in Chart I for pyridine and piperidine derivatives via the Grignard in early synthesis.

CHART I

Preparation of Pyridino and Piperidino Derivatives

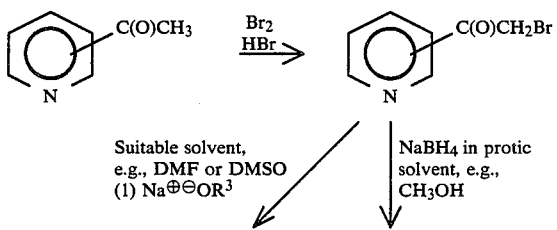

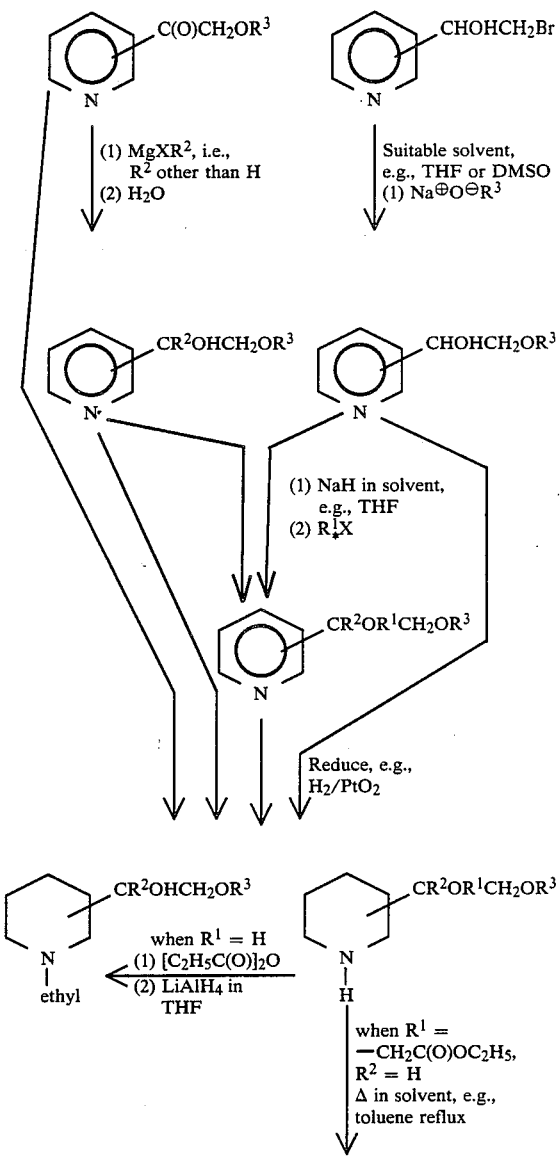

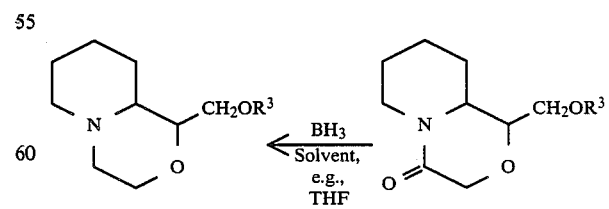

Footnotes to Chart I:

*$R^1$ = loweralkyl or carbethoxymethyl,

X = Cl or Br.

CHART II
Preparation of Pyrrolidine, Piperidine and Homopiperidine Derivatives (a)

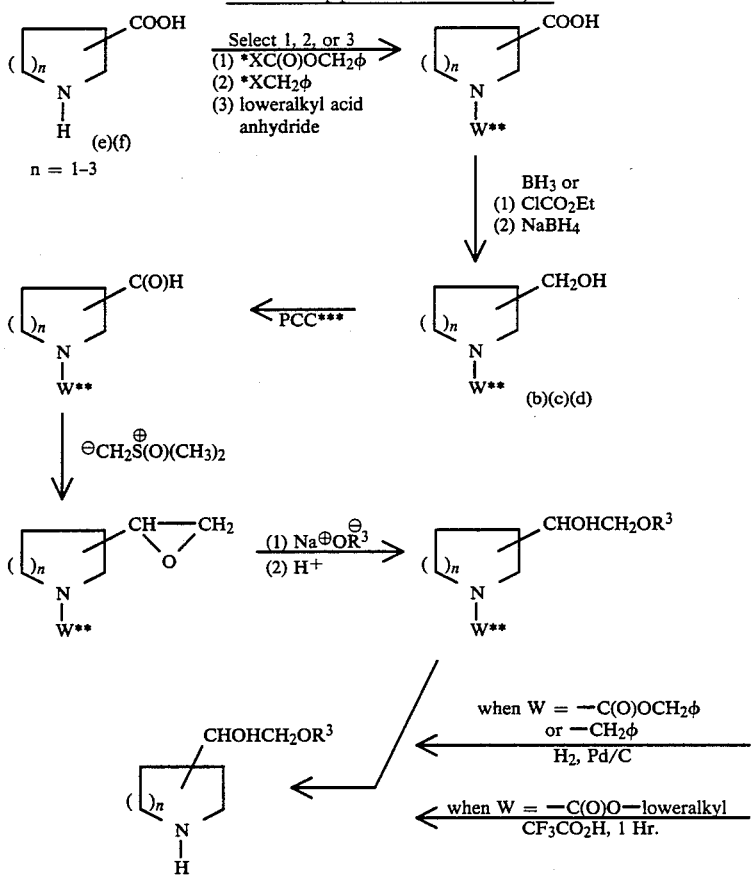

Footnotes Chart II:
*X = Cl, Br.
**W = —C(O)OCH$_2\phi$, —CH$_2\phi$ or —C(O)O—loweralkyl.
***PCC is pyridinium chlorochromate.
(a) Mori, M., et al, TETRAHEDRON (1985) 41, 5465.
(b) 3-Hydroxymethyl-1-loweralkyl or 1-benzylpyrrolidines as prepared in U.S. Pat. No. 3,318,908 may be used here.
(c) 3-Substituted-1-loweralkyl (or 1-benzyl) homopiperidines preparable by the method described in J. ORG. CHEM. 39, p. 893–902 may be used.
(d) 4-Homopiperidinone is known (Ger. patents 2,722,416; 2,617,101; 2,357,253) and may be converted to 4-hydroxymethyl-homopiperidine, as follows: Block homopiperidine N as above; reduce to 4-hydroxy; halogenate to 4-chloro treat with metal cyanide to give 4-cyano; reduce to 4-aminomethyl; treat with nitrous acid in methanol to give 4-hydroxymethyl-homopiperidine (Refer to U.S. Pat. No. 3,318,908 for method corresponding to preparation of 3-hydroxymethylpyrrolidine).
(e) 3-Carboxyhomopiperidine may be prepared by the method of P. Krogsgaard-Larsen et al in ACTA. CHEM. SCAND. B32, 327 (1978); 4-carboxy-homopyridine may be prepared by hydrolysis of 4-cyanohomopiperidine.
(f) 2,3- and 4-piperidinecarboxylic acids are available commercially as pipecolinic, nipecotic, and isonipecotic acids, respectively.

CHART III
Alternate Method of Preparing 2-Pyrrolidinyl, 2-Piperidinyl and 2-Homopiperidinyl Derivatives

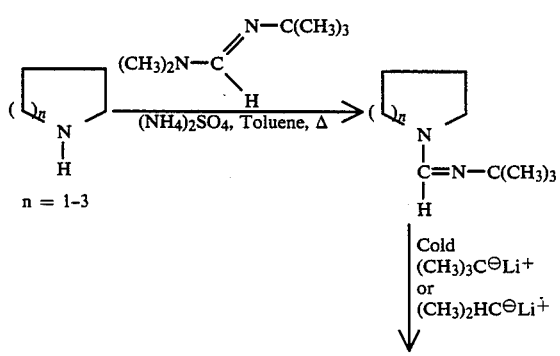

-continued
CHART III
Alternate Method of Preparing 2-Pyrrolidinyl, 2-Piperidinyl and 2-Homopiperidinyl Derivatives

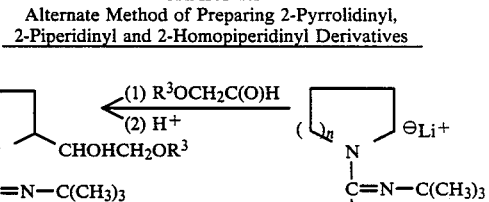

-continued
CHART III
Alternate Method of Preparing 2-Pyrrolidinyl, 2-Piperidinyl and 2-Homopiperidinyl Derivatives

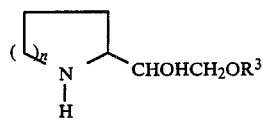

References:
(1) Meyers, A. I.; Edwards, P. D.; Ricker, W. F. and Bailey, T, R., J. AM. CHEM. SOC. (1984), 106 3270.
(2) Meyers, A. I.; Edwards, P. D.; Bailey, T. R. and Jagdmann, G. E., J. ORG. CHEM. (1985), 50 1019.

Other double ethers (i.e., $R^1$=loweralkyl) of the aryloxymethyl-pyrrolidine, piperidine or homopiperidinemethanol derivatives may be prepared from compounds wherein the heterocyclic nitrogen is blocked with benzyl and thereafter reacting with sodium hydride and a primary or secondary loweralkyl halide and thereafter debenzylating by hydrogenolysis with palladium on carbon as illustrated by the following equation.

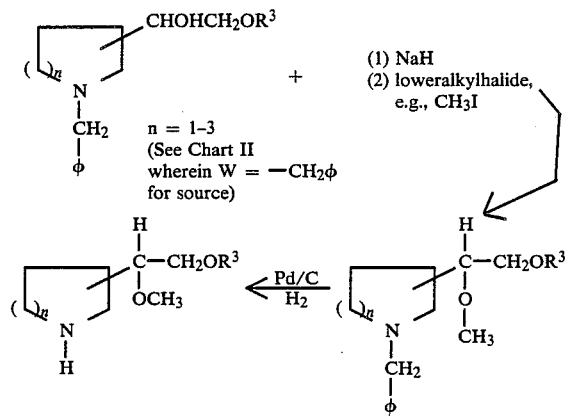

Certain compounds of Formula I may be alkylated on pyrrolidine, piperidine or homopiperidine nitrogen by using a 1:1 molar ratio of loweralkyl iodide under mildly basic conditions illustrated by the following equation:

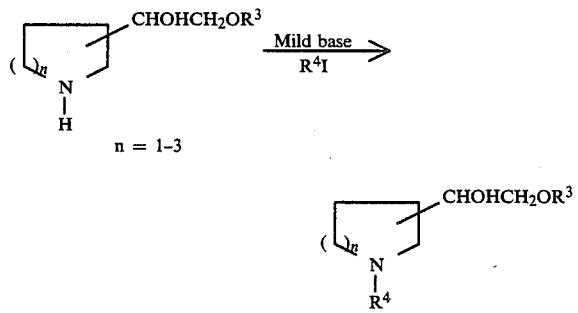

Certain compounds of Formula I may be alkylated on pyrrolidine, piperidine or homopiperidine nitrogen and on the hydroxy group as well by using a strong base; e.g., sodium hydride, along with 2 moles of loweralkyl halide; e.g., bromide, as illustrated by the following equation:

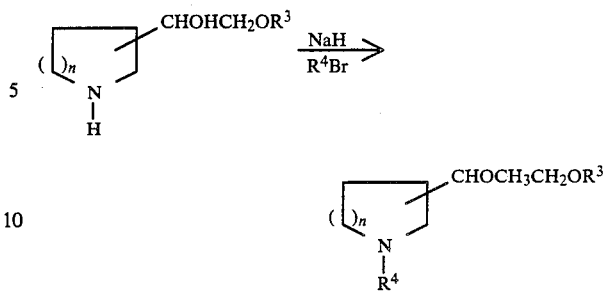

Compounds of Formula I wherein $R^3$ is aminophenyl may be prepared by reducing the corresponding nitro compound with iron powder and hydrochloric acid at about 25°–80° C.

Compounds of Formula I wherein $R^3$ is monomethylaminophenyl and Z is other than pyridino may also be prepared by reacting the corresponding 1-benzylaminophenyl compound with methyl chloroformate and reducing the urethane obtained with lithium aluminum hydride followed by debenzylating with palladium on carbon with hydrogen.

Compounds of Formula I wherein $R^3$ is dimethylaminophenyl may also be prepared by reacting the corresponding aminophenyl compound with more than 2 equivalents of formaldehyde and cyanoborohydride in a solvent such as acetonitrile under mildly acidic conditions as provided by the use of glacial acetic acid.

Compounds of Formula I wherein Z is pyridino and $R^3$ is monomethylaminophenyl may also be prepared by controlling the formaldehyde to 1 to 1.3 equivalents per mole of the amino-phenyl compound with cyanoborohydride in mildly acidic acetonitrile.

The preferred process for preparing pyridinyl and piperidinyl compounds of Formula I is comprised of the following steps:

Step 1, brominating a pyridine compound having the formula:

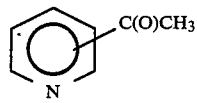

to give a compound having the formula:

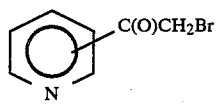

Step 2, reducing a compound prepared in Step 1 with sodium borohydride in protic solvent; e.g. methanol, to give a compound having the formula:

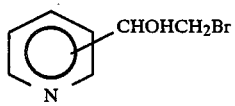

Step 3, reacting a compound prepared in Step 2 with a compound having the formula:

wherein R³ is an aryl group selected from 1 and 2-naphthalenyl, 2,3-dihydroinden-4 or 5 yl, phenyl, or phenyl substituted by p0 loweralkyl,
loweralkoxy,
halogen,
trifluoromethyl,
phenyl,
methylenedioxy,
nitro,
monomethylamino,
dimethylamino, or
loweracylamino
to give a compound having the formula:

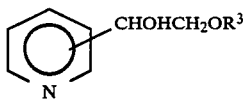

wherein R³ is the same as its starting value.

Step 4, When desired, reacting a compound prepared in Step 3 with sodium hydride in a suitable solvent; e.g., tetrahydrofuran, and a reagent having the formula:

R¹X wherein R¹ is loweralkyl or carbethoxymethyl and X is chlorine, bromine, or iodine to give a compound having the formula:

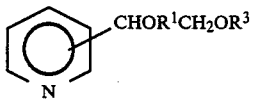

wherein R³ is as defined in Step 3 and R¹ is the same as in the reagent R¹X;

Step 5, reducing a compound prepared in Steps 3 or 4 with hydrogen over platinum oxide to give a compound having the formula:

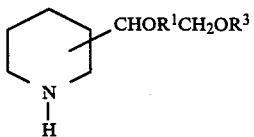

wherein R¹ is hydrogen, loweralkyl or carbethoxymethyl and R³ is as defined in Step 3.

The following examples serve to illustrate the preparation of the novel compounds useful in treating arrhythmias and hypertension in living animals in the methods and compositions of this invention. The scope of the invention is, however, not limited thereto. Structures are illustrated in Table 1.

EXAMPLE 1

α-Phenoxymethyl-2-piperidinemethanol hydrochloride [1:1]

A solution of α-phenoxymethyl-2-pyridinemethanol hydrochloride (20.22 g, 0.08 mole) in 425 ml of methanol was hydrogenated for 2.5 hr in the presence of 1 g of platinum oxide at room temperature. TLC analysis (in 5% methanol-methylene chloride) showed that all the pyridine compound had been converted to the piperidine derivatives. Removal of methanol furnished an oil. The oil was dissolved in methylene chloride-hexane mixture and treated with ethereal hydrogen chloride. The resulting salt was triturated with acetone and recrystallized from methylenechloride-hexane-diethyl ether to give 5.28 g (25.5% of a white crystalline solid, m.p. 165°–171° C.

Analysis: Calculated for $C_{13}H_{20}NO_2Cl$: C, 60.58; H, 7.82; N, 5.43; Found: C, 60.49; H, 7.62; N, 5.55.

EXAMPLE 2

2-(1-Methoxy-2-phenoxyethyl)piperidine hydrobromide [1:1]

A solution of 2-(1-methoxy-2-phenoxyethyl)pyridine hydrochloride (11.47 g, 0.043 mole) in 200 ml of methanol was prepared. To this was added 0.5 g of platinum oxide. This mixture was hydrogenated for three hours at room temperature. Thin layer chromatography (2.5% and 5.0% methanol-methylene chloride) showed that no starting material remained. The platinum oxide was removed by filtration, and removal of the methanol in vacuo gave a greenish oil. A solution of methylene chloride containing the product was then treated with a solution of methylene chloride saturated with hydrogen bromide. The solvent was removed in vacuo, and the residue was recrystallized from CH₃OH-ether to give 4.62 g (34%) of the high melting diastereomer; m.p. 219°–225° C. dec. and 0.95 g of low melting diastereomer; m.p. 170°–174° C. with decomposition.

Analysis: Calculated for $C_{14}H_{22}NO_2Br$: C, 53.17; H, 7.01; N, 4.43; Found (high melting): C, 52.94; H, 6.89; N, 4.51; Found (low melting): C, 52.98; H, 7.08; N, 4.30.

EXAMPLE 3

α-[(1-Naphthalenyloxy)methyl]-2-piperidinemethanol hydrochloride hydrate [1:1:0.25]

A solution of α-(1-naphthalenyloxymethyl)-2-pyridinemethanol hydrochloride (22.30 g, 0.0735 mole) in 425 ml of methanol was hydrogenated at room temperature with 1 g of platinum oxide for 2 hr. At this time all starting material (as determined by TLC analysis in 10% methanol-chloroform) had been consumed. The solution was filtered and the methanol was removed on the rotary evaporator to give a brown solid which was converted to the free base by treatment with dilute ammonium hydroxide. The free base was extracted into methylene chloride. A sample of the free base was recrystallized from methylene chloride-hexane to give a crystalline white solid (m.p. 104°–106° C.) which gave a correct elemental analysis. The remaining free base was converted to the hydrochloride salt by dissolving the free base in methanol and treating the solution with ethereal hydrogen chloride. This salt was recrystallized from methanol-diethyl ether to give 6.67 g (25.6%) of white crystalline solid, m.p. 171°–174° C.

Analysis: Calculated for $C_{68}H_{90}N_4O_9Cl_4$: C, 65.37; H, 7.26; N, 4.48; Found: C, 65.14; H, 7.15; N, 4.45.

EXAMPLE 4

α-[[(1H-2,3-Dihydroinden-4-yl)oxy]methyl]-2-piperidinemethanol fumarate [1:1]

A solution of α-[[(1H-2m3-dihydroindent-4-yl)oxy]methyl]-2-pyridinemethanol hydrochloride (26.20 g, 0.78 mole) in 450 ml of methanol was hydrogenated for 2¾ hr in the presence of 1 g of platinum oxide at room temperature. All starting material had been reduced at this time. The solution was filtered, and the solvent was removed on the rotary evaporator. The resulting oil was dissolved in methylene chloride and converted to the free base by extraction with 10% sodium hydroxide.

The free base was converted to the fumarate salt. This was recrystallized from methanol-ether to give the high melting diastereomer, m.p. 173.5°–175.5° C. as a white crystalline solid (2.10 gm, 7.0% yield).

The solvent was removed in vacuo and the residue was recrystallized from ethanol-ether to give 12.88 gm (43%) of white crystalline product, m.p. 163.5°–165.5° C. (low melting diastereomer).

(Low melting diastereomer)

Analysis: Calculated for $C_{20}H_{27}NO_6$: C, 63.64; H, 7.21; N, 3.71; Found: C, 63.55; H, 7.35; N, 3.69.

(High melting diastereomer)

Analysis: Calculated for $C_{20}H_{27}NO_6$: C, 63.64; H, 7.21; N, 3.71; Found: C, 63.54; H, 7.30; N, 3.69.

EXAMPLE 5

α-[(3,4-Dimethylphenoxy)methyl]-2-piperidinemethanol fumarate [1:0.5]

A solution of α-[(3,4-dimethylphenoxy)methyl]pyridine-2-methanol hydrochloride (11.2 g, 0.04 mole) in 200 ml of methanol was hydrogenated at room temperature with 1.4 g of platinum oxide for 1 hr. TLC analysis [10% methanol-benzene; 10% methanol-chloroform; 1-10-90 (ammonia-methanol-chloroform)] showed that all starting material had reacted. The solution was filtered. The methanol was removed on the rotary evaporator, and the resulting oil was converted to the free base with 10% sodium hydroxide and extracted into methylene chloride.

The methylene chloride was removed on the rotary evaporator, and the free base was converted to the fumarate salt in methanol using equivalent molar quantities of free base and fumaric acid. The salt was recrystallized from methanol-ethyl acetate to give 9.23 g (75.1%) of white crystalline product, m.p. 193°–194° C. with decomposition.

Analysis: Calculated for $C_{17}H_{25}NO_4$: C, 66.43; H, 8.20; N, 4.56; Found: C, 66.21; H, 8.21; N, 4.49.

EXAMPLE 6

α-[(2,6-Dimethylphenoxy)methyl]-2-piperidinemethanol hydrochloride [1:1]

A solution of α-[(2,6-dimethylphenoxy)methyl]pyridine-2-methanol hydrochloride (11.20 g, 0.04 mole) in 200 ml of methanol was hydrogenated at room temperature with 1.4 g of platinum oxide for 45 minutes. The solution was filtered and the methanol removed by rotary evaporator. Trituration with ethyl ether gave a white solid which was recrystallized from methanol-ethyl ether (and dried at 100° C. overnight) to give 7.81 g (67.5%) of white crystalline product, m.p. 178°–179° C. with decomposition.

Analysis: Calculated for $C_{15}H_{24}ClNO_2$: C, 63.04; H, 8.46; N, 4.90; Found: C, 62.90; H, 8.52; N, 4.84.

EXAMPLE 7

α-[(2-Ethoxyphenoxy)methyl]-2-piperidinemethanol oxalate [1:0.5]

A solution of α-[(2-ethoxyphenoxy)methyl]pyridine-2-methanol hydrochloride (17.20 g, 0.0583 mole) in 250 ml of methanol was hydrogenated at room temperature with 2.0 g of platinum oxide for 1½ hr. The solution was filtered, and the methanol was removed on the rotary evaporator to give a light yellow oil. This hydrochloride salt was converted to the free base with 10% sodium hydroxide and the free base extracted into methylene chloride. Removal of methylene chloride gave a white solid which after recrystallization from methanol-ethyl acetate had a m.p. of 126°–135° C. A crystalline oxalate salt was obtained by using equimolar quantities of the free base and oxalic acid. The oxalate salt was recrystallized twice from methanol-ethyl acetate to give 6.10 g (33.6%) of white crystalline product, m.p. 129°–132° C.

Analysis: Calculated for $C_{16}H_{24}NO_5$: C, 61.92; H, 7.79; N, 4.51; Found: C, 61.80; H, 7.82; N, 4.42.

EXAMPLE 8

α-[(2,4-Dimethylphenoxy)methyl]-2-piperidinemethanol fumarate [1:0.5]

A solution of α-[(2,4-dimethylphenoxy)methyl]pyridine-2-methanol hydrochloride (10.0 g, 0.0347 mole) in 200 ml of methanol was hydrogenated at room temperature with 1.4 g of platinum oxide for ½ hr. The methanol solution was filtered and solvent removed on the rotary evaporator. The resulting material was dissolved in water, made basic with 10% sodium hydroxide and the free base was extracted into methylene chloride. Removal of methylene chloride on the rotary evaporator gave a yellow oil. While standing overnight the oil crystallized to give a white solid (softens 75°–78° C., 78°–90° C. m.p.). The free base was dissolved in methanol and treated with a methanol solution of an equimolar quantity of fumaric acid. A crystalline white solid was obtained by adding ether, and upon recrystallization from methanol-ethyl ether, 5.81 g (52.9%) of crystalline white product was obtained, m.p. 208°–212° C. with decomposition.

Analysis: Calculated for $C_{17}H_{25}NO_4$: C, 66.43; H, 8.20; N, 4.56; Found: C, 66.13; H, 8.17; N, 4.46.

EXAMPLE 9

α-[(4-Chlorophenoxy)methyl]-2-piperidinemethanol fumarate [1:0.5]

A solution of α-[(4-chlorophenoxy)methyl]pyridine-2-methanol 9.90 g (0.04 mole) was converted to the hydrochloride salt by dissolving in methanol and treating with ethereal hydrogen chloride. The solvents were removed and the resulting brown oil was dissolved in 200 ml of methanol and hydrogenated at room temperature with 1.4 g of platinum oxide for 1 hr. The solution was filtered and the methanol removed by rotary evaporation. The resulting oil was partitioned between 10% sodium hydroxide and methylene chloride and the methylene chloride was removed in vacuo to give an oil.

While standing at room temperature overnight in an enclosed container, the oil (free base) slowly began to crystallize.

The free base was converted to the fumarate salt by using equimolar quantities of free base and fumaric acid, each was dissolved separately in methanol and then mixed. Addition of ether gave a white solid which was dried in vacuo overnight at 100° C. to give 3.87 g (30.8%) of product, m.p. 202°–203° C. with decomposition.

Analysis: Calculated for $C_{15}H_{20}ClNO_4$: C, 57.42; H, 6.42; N, 4.46; Found: C, 57.41; H, 6.41; N, 4.45.

EXAMPLE 10

α-[[(1,1'-Biphenyl-4-yl-oxy]methyl]-2-piperidinemethanol hydrochloride hydrate [1:1:0.25]

A solution of α-[[(1,1-biphenyl-4-yl)oxy]methyl]-2-pyridine methanol hydrochloride (30.71 g, 0.093 mole) was dissolved in 600 ml of methanol and hydrogenated for 3.5 hr at room temperature with 1.4 g of platinum oxide. The solution was filtered, and removal of methanol in vacuo gave a white solid. The white solid was recrystallized twice from methanol-diethyl ether and dried at 100° C. to give 15.52 g (49.4%) of a white crystalline solid, m.p. 182°–184° C. with decomposition.

Analysis: Calculated for $C_{76}H_{98}N_4O_9Cl_4$: C, 67.44; H, 7.30; N, 4.14; Found: C, 67.54; H, 7.22; N, 4.11.

EXAMPLE 11

N-[4-[2-Hydroxy-2-(2-piperidinyl)ethoxy]phenyl]acetamide

A solution of N-[4-[2-hydroxy-2-(2-pyridinyl)ethoxy]phenyl]acetate (6.8 g, 0.025 mole), previously converted to the hydrochloride salt with ethereal hydrogen chloride in 200 ml of glacial acetic acid was hydrogenated at room temperature for 2.5 hr in the presence of 1.4 g of platinum oxide. The reaction mixture was filtered, and the acetic acid removed on the rotary evaporator. The residue was dissolved in water, made basic with 10% sodium hydroxide and the free base extracted with methylene chloride. Removal of solvent gave a brown solid which upon tirturation with diethyl ether gave 3.3 g (48%) of a white solid, m.p., 137°–148° C.

Analysis: Calculated for $C_{15}H_{22}N_2O_3$: C, 64.73; H, 7.97; N, 10.06; Found: C, 64.41; H, 8.06; N, 9.91.

EXAMPLE 12

1-Ethyl-α-[[(1H-2,3-dihydroinden-4-yl)oxy]methyl]-2-piperidinemethanol maleate [1:1]

A solution of the free base of α-[[(1H-2,3-dihydroinden-4-yl)oxy]methyl]-2-piperidinemethanol (1.76 g, 0.0046 mole) was prepared in a mixture of 50 ml of acetic anhydride and 20 ml of pyridine. The solution was stirred for 3.5 hr at 90° C. and then overnight at room temperature. The solvent was removed in vacuo to give 2.44 g of a brown oil. A mass spectrum of this oil showed that the starting material had been converted to the diacetate. The brown oil was then dissolved in 50 ml of tetrahydrofuran which has been freshly distilled from lithium aluminum hydride. To this solution was added lithium aluminum hydride (0.64 g, 0.0175 mole). A vigorous reaction resulted immediately with liberation of hydrogen. This mixture was stirred for 5 hr under gentle reflux and then overnight at room temperature. The reaction was quenched by the slow addition of isopropanol followed by water. The reaction mixture was filtered by suction and then all solvents removed in vacuo to give 1.76 g of a brown oil. This oil was dissolved in methanol and the solution was treated with a methanolic solution containing an equivalent amount of maleic acid. Addition of diethyl ether caused crystallization of 1.50 g (80.41%) of a white crystalline solid, m.p. 172°–176° C. with decomposition (after drying overnight at 100° C.).

Analysis: Calculated for $C_{22}H_{31}NO_6$: C, 65.17; H, 7.71; N, 3.45; Found: C, 64.86; H, 7.71; N, 3.43.

EXAMPLE 13

α-(Phenoxymethyl)-2-pyridinemethanol hydrochloride [1:1]

A solution of sodium phenoxide was prepared by slowly adding, with stirring and under nitrogen, a solution of phenol (37.6 g, 0.4 mole) in 300 ml of tetrahydrofuran (THF) (distilled from lithium aluminum hydride) to a mixture of sodium hydride (50% dispersion in oil, 19.2 g, 0.4 mole washed with petroleum ether) in 500 ml of THF. This addition was made over a 3 hr period. After stirring for an additional 15 minutes, evolution of hydrogen ceased. 1-(2'-Pyridyl)-2-bromoethanol* hydrobromide (28.1 g, 0.1 mole) was added in solid portions over a period of 30 min. The solution was refluxed overnight. The THF was removed on the rotary evaporator and the resulting red oil partitioned between water and methylene chloride. The methylene chloride layer was then back-extracted with 5% sodium hydroxide. The methylene chloride was dried over anhydrous sodium sulfate and removed in vacuo to give a red oil. The oil was dissolved in methanol and converted to the hydrochloride salt by addition of ethereal hydrogen chloride. This salt was recrystallized from methanol-diethyl ether to give 10.15 g (40%) of white crystalline solid, m.p. 141°–143° C.

*This bromohydrin was prepared from 2-acetylpyridine by bromination followed by sodium borohydride reduction of the brominated acetylpyridine. The bromohydrin was isolated as the hydrobromide salt. See L. Polo Friz, *Farmco Ed. Sci.* 18 (12, 927–980, 1963).

Analysis: Calculated for $C_{13}H_{14}O_2NCl$: C, 62.03; H, 5.61; N, 5.56; Found: C, 61.90; H, 5.60; N, 5.62.

EXAMPLE 14

α-(1-Naphthalenyloxymethyl)-2-pyridinemethanol hydrochloride [1:1]

A solution of sodium naphthoxide was prepared by adding slowly with stirring and under nitrogen a solution of α-naphthol (50.62 g, 0.35 mole) in 300 ml of tetrahydrofuran (THF) to a suspension of 16.87 g of 50% sodium hydride (8.44 g, 0.35 mole) in 500 ml of THF. This addition was made over a 2 hr period. After stirring for an additional 15 minutes, evolution of hydrogen ceased. 1-(2'-Pyridyl)-2-bromoethanol* hydrobromide (24.5 g, 0.0878 mole) was added in solid portions over a 30 minute period, and the reaction mixture was refluxed overnight. The tetrahydrofuran was removed on the rotary evaporator, and the brown residue was dissolved in 600 ml of water. The aqueous phase was extracted with diethyl ether, and the ether layer was back-extracted with 10% sodium hydroxide. The ether layer was dried over anhydrous sodium sulfate, and the solvent was removed by rotary evaporator to give a brown oil. The oil was recrystallized from acetone-petroleum ether to give solid free base, m.p. 107°–108.5° C. The free base was dissolved in methylene chloride and converted to the hydrochloride salt by addition of ethereal hydrogen chloride with additional diethyl ether. The hydrochloride salt was obtained in yield of 13.24 g (50%) as a white crystalline solid, m.p. 181.5°–183° C. with decomposition.

Analysis: Calculated for $C_{17}H_{16}NO_2Cl$: C, 67.66; H, 5.34; N, 4.64; Found: C, 67.69; H, 5.37; N, 4.65.

*This bromohydrin was prepared from 2-acetyl-pyridine by bromination followed by sodium borohydride reduction of the brominated acetylpyridine.

EXAMPLE 15

α-{[(1H-2,3-Dihydroinden-4-yl)oxy]methyl}-2-pyridinemethanol hydrobromide [1:1]

A solution of the sodium salt of 4-indanol in tetrahydrofuran was prepared by the addition of a solution of 4-indanol (100.0 g, 0.747 mole) in 400 ml of tetrahydrofuran to sodium hydride (33.9 g, 0.747 mole) which was previously washed with hexane, dried under nitrogen atmosphere and suspended in 650 ml of tetrahydrofuran. The resulting solution was stirred an additional 0.5 hr (under nitrogen atmosphere) at room temperature. Evolution of hydrogen ceased. 1-(2'-Pyridyl)-2-bromoethanol* hydrobromide (56.6 g, 0.2 mole) was added in small solid portions over a period of 0.5 hr under nitrogen atmosphere. The resulting solution was stirred under reflux overnight (under nitrogen). The solution was filtered and the solvent was concentrated on the rotary evaporator. A liter of water was added and the mixture extracted with methylene chloride. The methylene chloride was back-extracted with sodium hydroxide. The methylene chloride was removed in vacuo to give a purple oil. This oil was dissolved in methanol and converted to the hydrobromide salt. The light brown solid which was obtained was recrystallized from methanoldiethyl ether to give 43.95 g (65.4%) of a light brown crystalline solid, m.p. 147°–148.5° C.

Analysis: Calculated for $C_{16}H_{18}NO_2Br$: C, 57.16; H, 5.40; N, 4.17; Found: C, 57.05; H, 5.36; N, 3.92.

*This bromohydrin was prepared from 2-acetylpyridine by bromination followed by sodium borohydride reduction of the brominated acetylpyridine.

EXAMPLE 16

α[(3,4-Dimethylphenoxy)methyl]pyridine-2-methanol hydrochloride [1:1]

A solution of sodium 3,4-dimethylphenoxide was prepared by adding slowly with stirring and under nitrogen a solution of 3,4-dimethylphenol (48.86, 0.4 mole) in 250 ml of tetrahydrofuran (distilled from lithium aluminum hydride) to a suspension of 50% sodium hydride (18.2 g, 0.4 mole) previously washed with hexane and in 250 ml of tetrahydrofuran. After stirring for 30 minutes at room temperature, all evolution of hydrogen ceased and 1-(2'-pyridyl)-2-bromoethanol* hydrobromide (28.3 g, 0.1 mole) was added all at once in solid form. The reaction mixture was refluxed under nitrogen overnight. The tetrahydrofuran was removed on the rotary evaporator, and the resulting oil was partitioned between water and methylene chloride. The methylene chloride layer was extracted with three 200 ml portions of 10% sodium hydroxide and dried over sodium sulfate. Removal of solvent gave a brown oil (23.82 g). This oil was dissolved in methanol and converted to the hydrochloride salt with ethereal hydrogen chloride. This salt was recrystallized from methanoldiethyl ether to give 16.20 g (57.9%) of an off-white crystalline solid, m.p. softens 161°–162° C., melts 163°–164° C. with decomposition.

Analysis: Calculated for $C_{15}H_{18}ClNO_2$: C, 64.40; H, 6.49; N, 5.01; Found: C, 64.41; H, 6.49; N, 4.93.

*This bromohydrin was prepared from 2-acetylpyridine by bromination in 48% hydrobromic acid followed by sodium borohydride reduction of the brominated acetylpyridine.

EXAMPLE 17

α-[(2,6-Dimethylphenoxy)methyl]-2-pyridinemethanol hydrochloride [1:1]

A solution of the sodium salt of 2,6-dimethylphenol was prepared by the addition of 2,6-dimethylphenol (48.86 g, 0.4 mole) in 300 ml of tetrahydrofuran to sodium hydride (19.2 g, 0.4 mole of 50% dispersion) which was previously washed with hexane and placed in 200 ml of tetrahydrofuran. The solution was stirred under nitrogen at room temperature for 0.5 hour; evolution of hydrogen ceased. 1-(2'-Pyridyl)-2-bromoethanol* hydrobromide (28.3 g, 0.1 mole) was added in small portions over 15 min as a solid. The mixture was refluxed under nitrogen overnight with stirring.

*This bromohydrin was prepared from 2-acetylpyridine by bromination followed by sodium reduction of the brominated acetylpyridine.

The reaction mixture was stripped of tetrahydrofuran and the resulting oil dissolved in 1 liter of water. The aqueous phase was extracted with methylene chloride and the methylene chloride phase was back-extracted with 10% sodium hydroxide. Removal of the methylene chloride gave a red oil which was converted to a solid hydrochloride salt by dissolving in methanol and treating with ethereal hydrogen chloride. The compound was recrystallized from methanol-diethyl ether to give 19.78 g (70%) of light brown crystalline solid, m.p. 163°–166° C. with decomposition.

Analysis: Calculated for $C_{15}H_{18}ClNO_2$: C, 64.40; H, 6.48; N, 5.00; Found: C, 64.48; H, 6.46; N, 4.90.

EXAMPLE 18

α-[(2-Ethoxyphenoxy)methyl]-2-pyridinemethanol hydrochloride [1:1]

A solution of the sodium salt of o-ethoxyphenol was prepared from 28.80 g (0.60 mole) of 50% sodium hydride and 82.90 g (0.60 mole) of o-ethoxyphenol in 500 ml of dimethylsulfoxide (dried over molecular sieves). The dark brown solution was stirred for one hr at room temperature (all under nitrogen). 1-(2'-Pyridyl)-2-bromoethanol* hydrobromide (42.45 g, 0.15 mole) was added all at once in solid form and the resulting solution was stirred under nitrogen overnight at 95° C. in an oil bath. The dimethylsulfoxide was removed by vacuum distillation to give a red oil. The red oil was dissolved in water and the mixture was extracted with methylene chloride. The methylene chloride was back extracted with 10% sodium hydroxide. Removal of methylene chloride gave a brown oil which was converted to the hydrochloride salt in methanol with ethereal hydrogen chloride. The salt was recrystallized from methanol-diethyl ether to give a white solid, m.p. 88°–92° C. The solid was dried under vacuum at 100° C. overnight to give 8.66 g (19.3%) of a crystalline white solid, m.p. 92°–94.5° C.

Analysis: Calculated for $C_{15}H_{17}ClNO_3$: C, 60.91; H, 6.13; N, 4.74; Found: C, 60.62; H, 6.13; N, 4.70.

*This bromohydrin was prepared from 2-acetylpyridine by bromination followed by sodium borohydride reduction of the brominated acetylpyridine.

EXAMPLE 19

α-[(4-Chlorophenoxy)methyl]-2-pyridinemethanol

A solution of the sodium salt of p-chlorophenol in dimethylsulfoxide was prepared by the addition of p-chlorophenol (76.80 g, 0.6 mole) in 450 ml of dimethylsulfoxide to a sodium hydride (50%) dispersion (28.80 g, 0.6 mole) in 450 ml of dimethylsulfoxide over 45 min.

The solution was then stirred for 1 hr at room temperature. 1-(2'-Pyridyl)-2-bromoethanol* hydrobromide (42.15 g, 0.15 mole) was added all at once and the solution was stirred overnight at 100° C. The dimethylsulfoxide was removed by vacuum distillation. The residue was then dissolved in water and the mixture was extracted with methylene chloride. The methylene chloride was back extracted with 10% sodium hydroxide, dried over anhydrous magnesium sulfate, and the solvent removed to give a reddish brown solid. The free base was recrystallized from ethanol-water to give 2.86 g (10.3%) of a light-brown solid, m.p. 90°-92° C.

Analysis: Calculated for $C_{13}H_{12}ClNO_2$: C, 62.53; H, 4.84; N, 5.61; Found: C, 62.42; H, 4.90; N, 5.19.

*This bromohydrin was prepared from 2-acetylpyridine by bromination followed by sodium borohydride reduction of the brominated acetylpyridine.

EXAMPLE 20

α-[(2,4-Dimethylphenoxy)methyl]-2-pyridinemethanol hydrochloride [1:1].

A solution of the sodium salt of 2,4-dimethylphenol was prepared in 500 ml of tetrahydrofuran (distilled from lithium aluminum hydride) by the addition of 2,4-dimethylphenol (68.40 g, 0.56 mole) to sodium hydride (26.88 g of a 50% dispersion, 0.58 mole) which had been washed with hexane and dried over nitrogen. The reaction mixture was then stirred under nitrogen for 0.5 hr and hydrogen evolution ceased. 1-(2'-Pyridyl)-2-bromoethanol* hydrobromide (39.18 g, 0.14 mole) was added all at once as a solid. The mixture was heated under nitrogen at reflux overnight. The following day the tetrahydrofuran was taken to dryness on a rotary evaporator. The residual oil was dissolved in 1 liter of water and then extracted with methylene chloride. The methylene chloride was back extracted with 10% sodium hydroxide. The methylene chloride layer was dried over anhydrous sodium sulfate, filtered, and the solvent removed to give a red oil. The oil was dissolved in methanol and was converted to the hydrochloride salt using ethereal hydrogen chloride. The solid was recrystallized from methanol-ethyl ether to give 17.03 g of white crystalline product, m.p. 136°-137° C.

Analysis: Calculated for $C_{15}H_{18}ClNO_2$: C, 64.40; H, 6.48; N, 5.01; Found: C, 64.40; H, 6.48; N, 4.96.

*This bromohydrin was prepared from α-acetylpyridine by bromination followed by sodium borohydride reduction of the brominated acetylpyridine.

EXAMPLE 21

α-{[(1,1'-Biphenyl-4-yl)oxy]methyl}-2-pyridinemethanol hydrochloride [1:1]

A solution of the sodium salt of p-phenylphenol in tetrahydrofuran (THF) was prepared by the addition of p-phenylphenol (102.0 g, 0.6 mole) in 250 ml of THF to sodium hydride (28.80 g, 50% dispersion, 0.60 mole) which was previously washed with hexane, dried in a stream of nitrogen and placed in 250 ml of THF. The resulting solution was stirred an additional 0.5 hr at room temperature. 1-(2'-Pyridyl)-2-bromoethanol* hydrobromide (42.15 g, 0.05 mole) was added as a solid all at once. The resulting mixture was refluxed overnight under nitrogen.

*This bromohydrin was prepared from 2-acetylpyridine by bromination followed by sodium bromohydride reduction of the brominated acetylpyridine.

The THF was removed on the rotary evaporator. The residue was dissolved in water (800 ml) and the mixture was extracted with methylene chloride. The methylene chloride was then back extracted with sodium hydroxide. The methylene chloride was dried over anhydrous sodium sulfate, filtered and methylene chloride was removed to give a dark brown solid. The brown solid was dissolved in methanol and converted to the hydrochloride salt with ethereal hydrogen chloride. This white product was recrystallized from methanol-diethyl ether to give 36.86 g (75.3%) of white crystalline product, m.p. 202°-205° C. with decomposition.

Analysis: Calculated for $C_{19}H_{18}ClNO_2$: C, 69.62; H, 5.53; N, 4.27; Found: C, 69.50; H, 5.52; N, 4.26.

EXAMPLE 22

N-[4-[2-Hydroxy-2-(2-pyridinyl)ethoxy]phenyl]acetamide

The sodium salt of p-hydroxyacetanilide was prepared by adding slowly with stirring under nitrogen a solution of p-hydroxyacetanilide (120.9 g, 0.8 mole) in 250 ml of dimethylsulfoxide (dried over molecular sieves) to a mixture of 50% sodium hydride (38.4 g, 0.8 mole) which was previously washed with petroleum ether and dried and subsequently placed in 250 ml of dimethylsulfoxide. The addition took place over one hour, and the reaction was then stirred for one hour at room temperature. 1-(2'-Pyridyl)-2-bromoethanol* hydrobromide (55.90 g, 0.2 mole) was added all at once, and the mixture was stirred for 1.5 hr at room temperature under nitrogen. The reaction mixture was then stirred overnight at 95° C. The solvent was removed then vacuum distilled by vacuum distillation. The residue was dissolved in 1 liter of water and the solution was extracted with methylene chloride. The methylene chloride was back extracted with 10% sodium hydroxide. The methylene chloride was dried over anhydrous sodium sulfate and the solvent removed to give 18.56 g of crude brown solid. This solid was triturated with diethyl ether and then recrystallized from isopropyl ether to give 8.51 g (15.6%) of light brown solid, m.p. 127.5°-129.0° C.

Analysis: Calculated for $C_{15}H_{16}N_2O_3$: C, 66.16; H, 5.92; N, 10.29; Found: C, 65.93; H, 5.88; N, 10.15.

* This bromohydrin was prepared from 2-acetylpyridine by bromination in 48% hydrobromic acid followed by sodium borohydride reduction of the brominated 2-acetylpyridine.

EXAMPLE 23

1-[(2-Ethoxyphenoxy)methyl]-6,7,8,9-tetrahydro-1H-pyrido[2,1-C][1,4-oxazin-4(3H)one A solution of 21.4 g (0.061 mole) of 2-[2-(2-ethoxyphenoxy)-1-(2-piperidinyl)ethoxy]acetic acid ethyl ester was dissolved in 200 ml of toluene and refluxed for 6 hr. Solvent was removed on the rotary evaporator, and the dark brown oil was dissolved in 200 ml of diethyl ether. The ether solution was extracted with 0.5M sulfuric acid. Evaporation of the ether gave a dark brown viscous oil which upon trituration with diisopropyl ether gave 8.17 g (43.8%) of white crystalline product; m,p. 66°-82° C. with decomposition (diastereomeric mixture).

Analysis: Calculated for $C_{17}H_{23}NO_4$: C, 66.86; H, 7.59; N, 4.59; Found: C, 66.72; H, 7.63; N, 4.55.

EXAMPLE 24

α-[(4-Nitrophenoxy)methyl]-2-pyridinemethanol hydrochloride [1:1]

A solution of the sodium salt of p-nitrophenol in dimethylsulfoxide was prepared by the addition of p-nitrophenol (198.09 g, 1.424 mole) in 800 ml of dimethylsulfoxide to sodium hydride (68.35 g, 50% dispersion, 1.424 mole), which was previously washed with hexane, dried in a stream of nitrogen and placed in 250 ml of dimethylsulfoxide. The resulting solution was stirred for 0.5 hr at room temperature. 1-(2'-Pyridyl)-2-bromoethanol* hydrobromide (100 g, 0.356 mole) was added as a solid over 25–30 min. The resulting mixture was stirred overnight at 95° C.

*This bromohydrin was prepared 2-acetylpyridine by bromination followed by sodium borohydride reduction of the brominated 2-acetylpyridine.

The dimethylsulfoxide was removed by vacuum distillation and a large excess of water was added. The aqueous phase was extracted with methylene chloride, and the methylene chloride was back extracted with 10% sodium hydroxide. The methylene chloride was dried over anhydrous sodium sulfate, filtered and methylene chloride removed to give a dark brown solid. The brown solid was triturated with ether to give 27.03 g (30%) of brown solid. Two grams of this brown solid was converted to the hydrochloride salt and a white crystalline product was obtained, m.p. 188°–190° C. with decomposition.

Analysis: Calculated for $C_{13}H_{13}ClN_2O_4$: C, 52.63; H, 4.42; N, 9.44; Found: C, 52.51; H, 4.38; N, 9.40.

EXAMPLE 25

α-[(2,6-Dimethylphenoxy)methyl]-3-pyridinemethanol hydrochloride [1:1]

A solution of the sodium salt of 2,6-dimethylphenol was prepared in 250 ml of dimethylsulfoxide (dried over Linde 4A molecular sieves) by the addition of 2,6-dimethylphenol (24.4 g, 0.2 mole) to sodium hydride (50%, 9.6 g, 0.2 mole). The sodium salt was stirred 1.5 hr at room temperature, all under nitrogen. 1-(3'-Pyridyl)-2-bromoethanol* hydrobromide (14.2 g, 0.05 mole) was added all at once in solid portions, and the reaction mixture was stirred overnight at 70° C. The dimethylsulfoxide was removed in vacuo, and the resulting residue was diluted to 2 liters with water and extracted with diethyl ether. The ether layer was extracted with several portions of 1N sulfuric acid. The acidic phase was made alkaline with 10% sodium hydroxide and extracted with methylene chloride. Removal of this solvent gave a dark brown oil which was converted to the hydrochloride salt. The salt was recrystallized from methanol-diethyl ether to give 2.5 g (17.9%) of a white crystalline solid, m.p. 125°–127° C.

Analysis: Calculated for $C_{15}H_{18}NO_2Cl$: C, 64.40; H, 6.46; N, 5.01; Found: C, 64.20; H, 6.49; N, 4.96.

*This bromohydrin was prepared from 3-acetylpyridine by bromination followed by sodium borohydride reduction of the brominated 3-acetylpyridine.

EXAMPLE 26

α-[(2,4-Dimethylphenoxy)methyl]-3-pyridinemethanol hydrochloride hydrate [1:1:0.5]

A solution of the sodium salt of 2,4-dimethylphenol was prepared in 500 ml of dimethylformamide by the addition of 2,4-dimethylphenol (73.2 g, 0.6 mole) to sodium hydride (19.2 g, 0.4 mole of 50%) which had been washed with hexane and dried in a nitrogen stream. The reaction mixture was stirred for 0.5 hr at room temperature.

1-(3'-pyridyl)-2-bromoethanol* hydrobromide (29.2 g, 0.1 mole) was added all at once as a solid. The reaction mixture was stirred overnight at 83° C. The dimethylformamide was then removed on the rotary evaporator, and a dark brown oil was obtained which was partitioned between chloroform and 10% sodium hydroxide. The chloroform was back extracted with 10% sodium hydroxide. This organic phase was dried over sodium sulfate, and solvent was removed to give a dark brown oil. This oil was dissolved in methanol and converted to the hydrochloride salt with ethereal hydrogen chloride. Recrystallization from methanol-diethyl ether gave 20.45 g (70.8%) of a white crystalline solid, m.p. 146.5°–148.5° C. with decomposition.

*This bromohydrin was prepared from 3-acetylpyridine by bromination followed by sodium borohydride reduction of the brominated 3-acetylpyridine.

Analysis: Calculated for $C_{30}H_{38}N_2O_5Cl_2$: C, 62.39; H, 6.63; N, 4.85; Found: C, 62.44; H, 6.33; N, 4.87.

EXAMPLE 27

α-[(2,4-Dimethylphenoxy)methyl]-4-pyridinemethanol hydrochloride [1:1]

A solution of the sodium salt of 2,4-dimethylphenol in 500 ml of dimethylformamide was prepared from sodium hydride (50%, 19.2 g, 0.4 mole) and 2,4-dimethylphenol (73.2 g, 0.6 mole). This solution was stirred for 1 hr at room temperature. 1-(4'-(Pyridyl)-2-bromoethanol* hydrobromide (29.2 g, 0.1 mole) was added, and the reaction mixture was stirred overnight at 85° C. The dimethylformamide was removed in vacuo. The residue was partitioned between chloroform and 10% sodium hydroxide. The chloroform layer was dried and filtered, and the solvent removed to give a dark brown oil. The oil was dissolved in methanol and converted to the hydrochloride salt with ethereal hydrogen chloride. Subsequent recrystallizations from methanoldiethyl ether gave 1.85 g of light brown solid (6.6%), m.p. 188°–189.5° C.

Analysis: Calculated for $C_{15}H_{18}NO_2Cl$: C, 64.39; H, 6.48; N, 5.00; Found: C, 63.91; H, 6.44; N, 5.10.

*This bromohydrin was prepared from 4-acetylpyridine by bromination followed by sodium borohydride reduction of the brominated 4-acetylpyridine.

EXAMPLE 28

α-(Phenoxymethyl)-3-pyridinemethanol hydrochloride [1:1]

A solution of the sodium salt of phenol was prepared in dimethylformamide (500 ml) (dried over Linde 4A molecular sieves) by the addition of phenol (56.47 g, 0.6 mole) to sodium hydride (50%, 19.2 g, 0.4 mole). The sodium-phenoxide was stirred under nitrogen for 1.5 hr at room temperature. 1-(3'-Pyridyl)-2-bromoethanol* hydrobromide (29.2 g, 0.1 mole) was added all at once as a solid, and the reaction was stirred overnight at 83° C. The dimethylformamide was removed in vacuo, and the residue was dissolved in chloroform and the solution was extracted with several portions of 10% sodium hydroxide. The chloroform was removed, and the residue was converted to the hydrochloride salt. The salt was recrystallized from methanoldiethyl ether to give 4.3 g (17.18%) of a light brown solid, m.p. 136°–138° C. with decomposition.

Analysis: Calculated for $C_{13}H_{14}NO_2Cl$: C, 62.03; H, 5.61; N, 5.56; Found: C, 62.02; H, 5.61; N, 5.59.

*This bromohydrin was prepared from 3-acetylpyridine by bromination followed by sodium borohydride reduction of the brominated 3-acetylpyridine.

EXAMPLE 29

α-[[(1,3-Benzodioxol-5-yl)oxy]methyl]pyridine-2-methanol hydrochloride [1:1]

A solution of sodium 3,4-methylenedioxy-phenoxide was prepared by adding slowly with stirring and under nitrogen a solution of 3,4-methylenedioxy-phenol (59.66 g, 0.432 mole) in 250 ml of tetrahydrofuran (THF) (distilled from lithium aluminum hydride) to a mixture of sodium hydride (50%) (20.74 g, 0.432 mole), (previously washed with hexane and dried) in 250 ml of THF. After stirring for 30 min at room temperature, all evolution of hydrogen ceased and 1-(2'-pyridyl)-2-bromoethanol* hydrobromide (30.56 g, 0.108 mole) was added as a solid over a 5 min period. The reaction was heated at reflux overnight under nitrogen. The THF was removed in vacuo, and the resulting dark brown oil was partitioned between water and methylene chloride. The methylene chloride layer was extracted with 10% sodium hydroxide and was dried over sodium sulfate. The solvent was removed in vacuo to give a brown solid (21.95 g). This material was dissolved in methanol and converted to the hydrochloride salt with ethereal hydrogen chloride. This salt was recrystallized from methanol-diethyl ether to give 18.29 g (57.3%) of a brown solid, m.p. 165.6°–167.0° C. with decomposition.

Analysis: Calculated for $C_{14}H_{14}ClNO_4$: C, 56.86; H, 4.77; N, 4.74; Found: C, 56.47; H, 4.86; N, 4.50.
*This bromohydrin was prepared from 2-acetylpyridine by bromination in 48% hydrobromic acid followed by sodium borohydride reduction of the brominated acetylpyridine.

EXAMPLE 30

α-[(2-Ethoxyphenoxy)methyl]-1-ethyl-2-piperidinemethanol maleate [1:1]

A solution of α-[(2-ethoxyphenoxy)methyl]-2-pyridinemethanol hydrochloride (10.0 g., 0.034 mole) in 150 ml of methanol was hydrogenated at room temperature for 2 hr in the presence of 1.40 g of platinum oxide. Solvent was removed by rotary evaporator and NMR showed that the desired piperidine compound was obtained (9.35 g). This hydrochloride salt was dissolved in 150 ml of water and the solution was made alkaline (pH=8) with sodium bicarbonate. The free base was extracted from this aqueous solution with methylene chloride. Removal of methylene chloride gave 6.73 g of α-[(2-ethoxyphenoxy)methyl]-2-piperidinemethanol. The entire amount of the piperidine-methanol derivative (6.73 g) was dissolved in a mixture of 50 ml of acetic anhydride and 50 ml of pyridine and the mixture was heated at 90° C. for 4 hr. The reaction mixture was then stirred overnight at room temperature. Excess acetic acid anhydride and pyridine were removed in vacuo. The sample was then pumped under vacuum to remove final traces of pyridine and acetic anhydride. Formation of the diacetate derivative was confirmed by mass spectral analysis. The diacetate (9.82 g, 0.03 mole, as a viscous oil) was dissolved in 100 ml of tetrahydrofuran. To this solution was added slowly and under nitrogen with stirring, lithium aluminum hydride (3.06 g, 0.078 mole). Vigorous evolution of hydrogen occurred. The reaction mixture was stirred for 2.5 hr at room temperature and then slowly quenched with isopropanol followed by water. The reaction mixture was filtered and washed with methanol. The solvent was removed in vacuo, and the resulting oil was then partitioned between water and chloroform. The chloroform was removed in vacuo to give 5.42 g of light brown oil. The maleate salt was prepared by mixing equimolar methanol solutions of the free base and maleic acid. Addition of diethyl ether caused crystallization of a solid. The solid was triturated with isopropyl ether followed by ethyl acetate to give 2.24 g (16.1%) of a brown solid, m.p. 111.5°–115.0° C.

Analysis: Calculated for $C_{21}H_{31}NO_7$: C, 61.60; H, 7.63; N, 3.42; Found: C, 61.30; H, 7.52; N, 3.51.

EXAMPLE 31

1-[(2-Ethoxyphenoxy)methyl]octahydropyrido[2,1-c][1,4]oxazine

In 300 ml of tetrahydrofuran (freshly distilled from lithium aluminum hydride) was dissolved 1-[(2-ethoxyphenoxy)methyl]-6,7,8,9-tetrahydro-1H-pyrido[2,1-c][1,4]oxazin-4(3H)-one (8.12 g, 0.0265 mole). The solution was cooled to 5° C. in an ice bath and 40 ml of 1M borane in tetrahydrofuran was added by syringe to the stirred solution under nitrogen. The solution was stirred at room temperature for 2 hr and then heated at reflux for 2 hr. The reaction mixture was cooled to room temperature and slowly quenched with glacial acetic acid. The solvent was removed in vacuo. The residue was partitioned between 10% sodium hydroxide and diethyl ether. Removal of the diethyl ether gave a yellow oil. This oil was then dissolved in a minimum amount of chloroform and chromatographed on a 500 g. Silica Gel column (gradient elution with chloroform methanol). Fractions from the column were combined which gave a single spot on TLC (methanol-chloroform) at similar Rf. A total of 5.08 g (65.8%) of a light yellow oil was obtained.

Analysis: Calculated for $C_{17}H_{25}NO_3$: C, 70.07; H, 8.65; N, 4.81; Found: C, 70.32; H, 8.71; N, 4.72.

EXAMPLE 32

α-[(2-Chlorophenoxy)methyl]-2-piperidine methanol fumarate [1:0.5]

A solution of α-[(2-chlorophenoxy)methyl]-2-pyridinemethanol hydrochloride (5.01 g, 0.02 mole) in 100 ml of methanol was hydrogenated for 1.3 hr at room temperature in the presence of 1.4 g of platinum oxide. The solution was filtered and the solvent was removed in vacuo to give a brown gum. The residue was partitioned between methylene chloride and 10% sodium hydroxide. Removal of methylene chloride in vacuo gave a dark brown oil which crystallized in the flask. The brown solid was dissolved in methanol and treated with an equal molar quantity of fumaric acid. Addition of diethyl ether resulted in the formation of 1.90 g (30.2%) of gray crystalline solid, m.p. 181°–182° C. with decomposition.

Analysis: Calculated for $C_{15}H_{20}ClNO_4$: C, 57.42; H, 6.43; N, 4.46; Found: C, 57.64; H, 6.52; N, 4.38.

EXAMPLE 33

α-Methoxy-α-(phenoxymethyl)-α-(2-pyridinyl)methane

A mixture of sodium hydride (washed with hexane 50%, 3.6 g, 0.075 mole) in tetrahydrofuran (THP) (300 ml) was prepared. α-Phenoxymethyl-2-pyridinemethanol (16.2 g, 0.075 mole) in THF was added dropwise under nitrogen with stirring over 20 min. The resulting solution was stirred 1 hr at room temperature. Methyl iodide (11.65 g, 0.0825 mole) in 100 ml of THF was added dropwise over 20 min and the solution was stirred overnight at room temperature. The solvent was removed by rotary evaporator, and the oil obtained was partitioned between diethyl ether and water. Removal of ether gave 16.38 g (95.5%) of α-methoxy-α-(phenoxymethyl)-60 -(2-pyridinyl)methane as a dark oil. The structure was confirmed by NMR.

EXAMPLE 34

2-[2-(2-Ethoxyphenoxy)-1-(2-piperidinyl)ethoxy]acetic acid ethyl ester

A mixture of sodium hydride (50%, 9.79 g, 0.204 mole, washed with hexane) in tetrahydrofuran (THF) was prepared. α-[(2-Ethoxyphenoxy)methyl]-2-pyridinemethanol (52.96 g, 0.204 mole) in 175 ml of THF was added dropwise under nitrogen with stirring over ½ hr. Stirring was continued for 1 hr at room temperature. Ethyl chloroacetate (24.98 g, 0.204 mole) in THF was added dropwise over 10 min. The resulting solution was heated at reflux for 2 hr and stirred at room temperature (72 hr). THF was removed, and the residue partitioned between diethyl ether and water. Removal of diethyl ether gave 57.9 g (0.168 mole, 82.4% yield) of the desired 2-[2-(2-ethoxy-phenoxy)-1-(2-pyridinyl)ethoxy]acetic acid ethyl ester as an oil. This structure of the product was confirmed by NMR.

This pyridine compound (5.18 g, 0.015 mole) was dissolved in the minimal amount of methanol and converted to the hydrochloride salt via ethereal hydrogen chloride. All solvents were removed and the volume was adjusted to 100 ml using methanol. To this methanol solution was added 1.4 g of platinum oxide and the reaction mixture was hydrogenated for 1 hr at room temperature. The methanol was removed by rotary evaporator and the residue was partitioned between dilute base and methylene chloride. Removal of methylene chloride gave 3.15 g (60% of the title compound as a red oil.

EXAMPLE 35

α-Methyl-α-phenoxymethyl-2-pyridinemethanol hydrochloride

2-Acetylpyridine is reacted with dimethyloxosulfonium methylide in THF at 25° C. for 2 hr. The reaction is quenched in water, and the aqueous mixture is extracted with methylene chloride. The methylene chloride solution is dried over sodium sulfate and the solvent is removed in vacuo. The residue is reacted with sodium phenoxide in THF to give the free base of the title compound which is reacted with ethereal hydrogen chloride to give a precipitate, the title compound.

EXAMPLE 36

α-Phenoxymethyl-α-phenyl-3-pyridinemethanol hydrochloride

2-Benzoylpyridine is reacted with dimethyloxosulfonium methylide in tetrahydrofuran (THF) at 25° C. for 2 hr. The reaction is quenched in water and the aqueous mixture is extracted with methylene chloride. The methylene chloride solution is dried over sodium sulfate and the solvent is removed in vacuo. The residue is reacted with sodium phenoxide in THF to give the free base of the title compound which is reacted with ethereal hydrogen chloride to give a precipitate, the title compound.

EXAMPLE 37

When in the procedure of Example 1 the following are hydrogenated in the presence of platinum oxide:
α-methyl-α-phenoxymethyl-2-pyridine methanol hydrochloride, and
α-phenoxymethyl-α-phenyl-3-pyridine methanol hydrochloride,
there are obtained
α-methyl-α-phenoxymethyl-2-piperidinemethanol hydrochloride, and
α-phenoxymethyl, α-phenyl-3-piperidinemethanol hydrochloride.

EXAMPLE 38

α-(Phenoxymethyl)-2-pyrrolidinemethanol hydrochloride [1:1]

2-(Formyl)-1-pyrrolidinecarboxylic acid phenylmethyl ester is prepared from 2-(hydroxymethyl)-1-pyrrolidinecarboxylic acid phenyl methyl ester using pyridinium chlorochromate as described by Mori, M. in Tetrahedron (1985), 5465–5475, and converted to the corresponding 2-epoxide using dimethyloxosulfonium methylide obtained by mixing trimethyl sulfoxonium iodide and sodium hydride in an aprotic solvent. This epoxide is reacted with sodium phenoxide and the reaction mixture is acidified to give 2-(1-hydroxy-2-phenoxyethyl)-1-pyrrolidinecarboxylic acid phenyl ester which is hydrogenated over palladium on carbon to give the free base of the title compound. The free base after isolation is dissolved in methylene chloride-hexane mixture and treated with ethereal hydrogen chloride and the hydrochloride salt is recovered as in Example 1.

EXAMPLE 39

α-Phenoxymethyl-3-pyrrolidinemethanol hydrochloride [1:1]

1-Phenylmethyl-3-formylpyrrolidine is prepared from 1-phenylmethyl-3-hydroxymethyl pyrrolidine (source: method of U.S. Pat. No. 3,318,908) by reacting it with pyridinium chlorochromate and converted to the corresponding 3-epoxide using dimethyloxosulfonium methylide obtained by mixing trimethylsulfoxonium iodide and sodium hydride in aprotic solvent. The epoxide is reacted with sodium phenoxide and the reaction mixture is acidified to give 1-phenylmethyl-α-phenoxymethyl-2-pyrrolidinemethanol which is hydrogenated over palladium on carbon to give the free base of the title compound. The free base is converted to the hydrochloride salt as in Example 38.

EXAMPLE 40

1-Methyl-α-(phenoxymethyl)-3-pyrrolidinemethanol maleate [1:1]

1-Methyl-3-formylpyrrolidine is prepared from 1-methyl-3-hydroxymethylpyrrolidine (source: method of U.S. Pat. No. 3,318,908) by reacting it with pyridinium chlorochromate and converted to the 3-epoxide using dimethyloxosulfonium methylide obtained by mixing trimethyl sulfoxonium iodide and sodium hydride in aprotic solvent. The epoxide is reacted with sodium phenoxide and the mixture is acidified to give 1-(phenylmethyl)-α-(phenoxymethyl)-2-pyrrolidinemethanol which is hydrogenated over palladium on carbon to give the free base of the title compound. The maleate salt is prepared by mixing equimolar solutions of the free base and maleic acid in methanol.

EXAMPLE 41

α-Phenoxymethyl-2-homopiperidinemethanol hydrochloride

The N-tert-butyl formamidine derivative of homopiperidine is prepared and reacted with butyl lithium to produce the 2-metalated product [see Chart III; J. Org. Chem. (1985) 50, 1019, and J. Am. Chem. Soc. (1984) 106, 3270]. This metalated homopiperidine derivative is reacted with phenoxyacetaldehyde and the reaction mixture is acidified to give 1-(tert-butyl formamidinyl)-α-(phenoxymethyl)-homopiperidinemethanol which is isolated and heated in an aqueous methanolic solution of potassium hydroxide to give the free base of the title compound. The free base is converted to the hydrochloride salt by reacting with ethereal hydrogen chloride.

EXAMPLE 42

α-Phenoxymethyl-3-homopiperidinemethanol hydrochloride

3-Carboxyhomopiperidine (Source: U.S. Pat. No. 4,409,146) is reacted with benzoxycarbonyl chloride to give 3-(carboxy)-1-homopiperidinecarboxylic acid phenylmethyl ester. This derivative is isolated and reacted with diborane in tetrahydrofuran to give 3-(hydroxymethyl)-1-homopiperidinecarboxylic acid phenylmethyl ester. This derivative is isolated and reacted with pyridinium chlorochromate to give 3-(formyl)-1-homopiperidine carboxylic acid phenylmethyl ester. The epoxide of this derivative is prepared by reacting with trimethyl sulfoxonium iodide and sodium hydride in an aprotic solvent. This epoxide is reacted with sodium phenoxide and the reaction mixture is acidified to give 2-(1-hydroxy-2-phenoxyethyl)-1-homopiperidinecarboxylic acid phenylmethyl ester which is hydrogenated over palladium on carbon to give the free base of the title compound. The free base is then converted to the hydrochloride salt as in Example 38.

EXAMPLE 43

α-Phenoxymethyl-4-homopiperidinemethanol

4-Homopiperidinone (Source: Ger. Pat. Nos. 2,722,416; 2,717,101; and 2,357,253) is converted to the title compound by methods illustrated by the following series of equations:

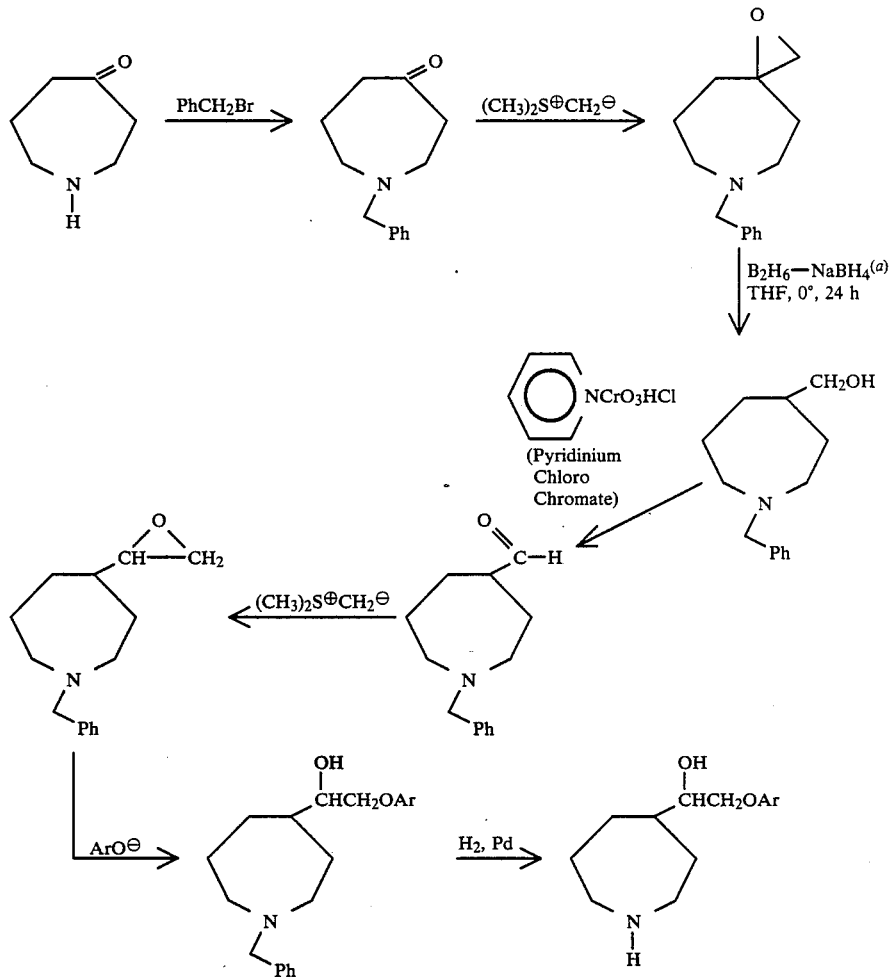

(a)Fieser, M; Fieser, L.; Reagents for Organic Synthesis; Wiley - Interscience, New York, 1969; Vol. 2, p 108.

EXAMPLE 44

1-Ethyl-α-phenoxymethyl-2-homopiperidine methanol

The free base of the title compound is prepared by reacting α-phenoxymethyl-2-homopiperidinemethanol with acetic anhydride and following the procedure of Example 12.

TABLE 1

$$Z-\underset{\underset{OR^1}{|}}{\overset{\overset{R^2}{|}}{C}}-CH_2OR^3$$

| Example No. | Z | R$^1$ | R$^2$ | R$^3$ | Salt |
|---|---|---|---|---|---|
| 1 | 2-piperidinyl | H | H | —C$_6$H$_5$ | HCl |
| 2 | 2-piperidinyl | —CH$_3$ | H | —C$_6$H$_5$ | HBr |
| 3 | 2-piperidinyl | H | H | —C$_{10}$H$_7$$^a$ | HCl, ¼H$_2$O |
| 4 | 2-piperidinyl | H | H | —C$_9$H$_9$$^b$ | fumarate |
| 5 | 2-piperidinyl | H | H | 3,4-(CH$_3$)$_2$—C$_6$H$_3$— | ½ fumarate |
| 6 | 2-piperidinyl | H | H | 2,6-(CH$_3$)$_2$—C$_6$H$_3$— | HCl |
| 7 | 2-piperidinyl | H | H | 2-OC$_2$H$_5$—C$_6$H$_4$— | ½ oxalate |
| 8 | 2-piperidinyl | H | H | 2,4-(CH$_3$)$_2$—C$_6$H$_3$— | ½ fumarate |
| 9 | 2-piperidinyl | H | H | 4-Cl—C$_6$H$_4$— | ½ fumarate |
| 10 | 2-piperidinyl | H | H | 4-C$_6$H$_5$—C$_6$H$_4$— | HCl, ¼H$_2$O |
| 11 | 2-piperidinyl | H | H | 4-NH—C(O)CH$_3$—C$_6$H$_4$— | — |
| 12 | 1-C$_2$H$_5$—2-piperidinyl | H | H | —C$_9$H$_9$$^b$ | maleate |
| 13 | 2-pyridinyl | H | H | —C$_6$H$_5$ | HCl |
| 14 | 2-pyridinyl | H | H | —C$_{10}$H$_7$$^a$ | HCl |
| 15 | 2-pyridinyl | H | H | —C$_9$H$_9$$^b$ | HBr |
| 16 | 2-pyridinyl | H | H | 3,4-(CH$_3$)$_2$—C$_6$H$_3$— | HCl |
| 17 | 2-pyridinyl | H | H | 2,6-(CH$_3$)$_2$—C$_6$H$_3$— | HCl |
| 18 | 2-pyridinyl | H | H | 2-OC$_2$H$_5$—C$_6$H$_4$— | HCl |
| 19 | 2-pyridinyl | H | H | 4-Cl—C$_6$H$_4$— | — |
| 20 | 2-pyridinyl | H | H | 2,4-(CH$_3$)$_2$—C$_6$H$_3$— | HCl |
| 21 | 2-pyridinyl | H | H | 4-C$_6$H$_5$—C$_6$H$_4$— | HCl |
| 22 | 2-pyridinyl | H | H | 4-NHC(O)CH$_3$—C$_6$H$_4$— | — |
| 23 | (fused piperidine-morpholinone structure) | — | — | 2-OC$_2$H$_5$—C$_6$H$_4$— | — |
| 24 | 2-pyridinyl | H | H | 4-NO$_2$—C$_6$H$_4$— | HCl |
| 25 | 3-pyridinyl | H | H | 2,6-(CH$_3$)$_2$—C$_6$H$_3$— | HCl |
| 26 | 3-pyridinyl | H | H | 2,4-(CH$_3$)$_2$—C$_6$H$_3$— | HCl, ½H$_2$O |
| 27 | 4-pyridinyl | H | H | 2,4-(CH$_3$)$_2$—C$_6$H$_3$— | HCl |
| 28 | 3-pyridinyl | H | H | C$_6$H$_5$— | HCl |
| 29 | 2-pyridinyl | H | H | (benzodioxole group) | HCl |
| 30 | 1-C$_2$H$_5$—2-piperidinyl | H | H | 2-OC$_2$H$_5$—C$_6$H$_4$— | maleate |
| 31 | (fused piperidine-morpholine structure) | — | — | 2-OC$_2$H$_5$—C$_6$H$_4$— | — |
| 32 | 2-piperidinyl | H | H | 2-Cl—C$_6$H$_4$— | ½ fumarate |
| 33 | 2-pyridinyl | —CH$_3$ | H | C$_6$H$_5$— | — |
| 34 | 2-piperidinyl | —CH$_2$C(O)OC$_2$H$_5$ | H | 2-OC$_2$H$_5$—C$_6$H$_4$— | — |
| 35 | 2-pyridinyl | H | —CH$_3$ | —C$_6$H$_5$ | HCl |
| 36 | 3-pyridinyl | H | —C$_6$H$_5$ | —C$_6$H$_5$ | HCl |
| 37a | 2-piperidinyl | H | —CH$_3$ | —C$_6$H$_5$ | HCl |
| $^b$ | 3-piperidinyl | H | —C$_6$H$_5$ | —C$_6$H$_5$ | HCl |
| 38 | 2-pyrrolidinyl | H | H | —C$_6$H$_5$ | HCl |
| 39 | 3-pyrrolidinyl | H | H | —C$_6$H$_5$ | HCl |
| 40 | 1-methyl-3-pyrrolidinyl | H | H | —C$_6$H$_5$ | maleate |
| 41 | 2-homopiperidinyl | H | H | —C$_6$H$_5$ | HCl |
| 42 | 3-homopiperidinyl | H | H | —C$_6$H$_5$ | HCl |
| 43 | 4-homopiperidinyl | H | H | —C$_6$H$_5$ | HCl |

TABLE 1-continued

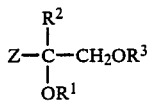

| Example No. | Z | R¹ | R² | R³ | Salt |
|---|---|---|---|---|---|
| 44 | 1-ethyl-4-homopiperidinyl | H | H | —C$_6$H$_5$ | HCl |

Footnotes:
[a] 1-naphthalenyl
[b] 1H—2,3-dihydroinden-4-yl

Pharmacology

The action of compounds of this invention in correcting cardiac arrhythmias or preventing cardiac arrhythmias is demonstrated by the following procedures:

Ouabain Induced Arrhythmias

Correction of existing cardiac arrhythmias of ventricular origin is carried out on (1) adult mongrel dogs which are under barbiturate anesthesia during the test. A Grass Model 7 polygraph was used for recording femoral arterial blood pressure (Statham P23AC transducer) and the electrocardiogram (grass 7P4 preamplifier). Ouabain was given intravenously in an initial dose of 40 μg/kg and in a second sose of 20 μg/kg 30 minutes after the first dose and in subsequent doses of 10 μg/kg which were repeated at 15 min intervals as required for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentration of compound was adjusted according to the weight of the dog to allow a volume infusion of 1 ml/min. The compound was considered to be active as an antiarrhythmic agent if reversion to a sinus rhythm occurred which was maintained for at least 30 minutes.

Correcting doses for several of the more active prepared compounds tested ranged from about 2–16 mg/kg in the Ouabain test.

Test Method for Antihypertensive Effect of Orally Administered Drugs to Unanesthetized Spontaneously Hypertensive Rats

Surgical Preparation of Rats

Charles River, spontaneously hypertensive rats, are anesthetized with sodium pentobarbital (50 mg/kg, IP). The abdomen and the top of head are shaved and cleaned. A midline incision, approximately 5 mm long, is made in the skin of the dorsal surface of the animal's neck. Brass tubing, 22 cm long with a slight bend in the end, is passed through the incision, under the skin diagonally down the animal's back and around to the right side of the lower abdomen of the rat.

The animal is then taped to the table in a supine position. A midline incision approximately 4 cm long is made with scissors in the skin and another through the abdominal muscle wall. With small blunt hemostats, the skin is separated from the abdominal muscle at the midline to expose the tip of the brass tube. A small opening is made through the abdominal muscle at the appropriate angle with the blunt tips of the hemostats.

The distal end of a modified Week's cannula is inserted in the abdominal cavity and the other end is threaded through the brass tube until it exits at the base of the animal's neck. The brass tubing is removed and the 7 mm cured polyethylene tip of the cannula is aligned and positioned for insertion into the abdominal aorta. The positioned cannula is filled with isotonic saline.

The abdominal viscera is gently moved to the side, exposing the aorta in the region of bifurcation. The aorta is isolated and 2 silk ligatures, 1 to 1.5 cm apart, are placed around it. The ligatures are used to briefly and gently occlude blood flow. The abdominal aorta is punctured craniad to the bifurcation with the tip of a 23 gauge hypodermic needle. The needle is removed and the tip of the cannula inserted through this opening toward the heart. Caution is taken to keep the tip vertically aligned in the aorta. Blood is allowed to flow back through the cannula to check correct insertion. The cannula is cleared of blood with a 0.4 cc flush of isotonic saline. The stability of the cannula in the artery is ensured by suturing the ligature tied around the cannula to the dorsal muscle layers lying directly beside the aorta. The cannula is also sutured to the abdominal wall at the point of exit. The abdominal viscera is repositioned and the abdominal wall and skin sutured in separate layers with blanket stitch. The animal is given 0.2 ml Combiotic ® (procaine penicillin G and dihydrostreptomycin sulfate).

The end of the cannula exteriorized at the base of the neck is tied off and passed through an L-shaped piece of aluminum tubing fastened to the skull by screws and dental cement (Purdy and Ashbrook, 1978), J. Pharm. Pharmacology 30: 436–41.

For protection and attachment of the cannula to the cage, the cannula is inserted through a length of flexible metal spring, which is attached to the aluminum tubing and to a part of a swivel device that permits the animal to move with relative freedom around the cage. During recovery, each rat is given a bottle of 5% dextrose containing terramycin (1 tsp. Pfizer Terramycin soluble powder/L 5% dextrose) to drink.

Blood Pressure Recordings

On the day following surgery, the tied-off cannula is reopened and attached to the swivel device. One end of a saline filled length of polyethylene 50 tubing is attached to the swivel and the other to a Statham pressure transducer (Model P23ID) creating a continuous saline-arterial connection. Continuous tracings from the direct aortic blood pressure are recorded on a Grass polygraph (Model 7). Heart rate is determined from the blood pressure pulse.

The electrical output of the blood pressure signal from the polygraph is fed into a Buxco Channel Cardiovascular analyzer (Model 12). The blood pressure signals are averaged for a 1-min period and measurements of blood pressure and heart rate is printed on a Texas Instruments data terminal (Model 700 ASR).

Maintenance of Rats

To maintain potency of cannula and to permit the animal to be used for maximum time, animals are continuously infused with heparin in sterile saline (2 mg/ml) at a rate of 0.05 to 0.06 ml/hr. Purina Mouse Chow and water are available ad libitum. A solution containing 5% dextrose and terramycin is given once weekly. Surgically prepared rats may be used more than once during a study. A minimum of 3 days must lapse before rats are used again. A rat is used only once in a dosage group.

Experimental Procedure—Blood Pressure

Test drugs were prepared as solutions using appropriate vehicles to attain solubility. Test drugs were administered to each of three rats directly through the intra-arterial catheter to achieve immediate placement of the drug into the cardiovascular circulation. An initial dose of 1 mg of the free base of test drug per kg of test subject's body weight was administered and the mean arterial blood pressure (MABP) was recorded prior to and at 5, 10, 15 and 30 minutes after test drug administration.

A second dose of the same test drug was then administered at a dose of 10 mg of free base per kg test subject's weight by the same route of administration (i.e., intraarterial) and measurements of the MABP was recorded prior to and at 5, 10, 15, 30, 60, 120, 180, 240, 300 and 360 minutes and 24 hr after administration of the test drug each test animal served as its own control and the absolute change from predose levels in MABP (mm Hg) induced by each test drug was determined for each time interval.

The results were expressed as the average change in MABP (mm Hg) for three rats. A decrease in MABP greater than or equal to 15 mm Hg at any post-test drug administration interval is regarded as an acceptable (active) antihypertensive effect. Compounds such as those of Examples 5, 6, 17, 20, 25, 26, 29 and 31 were considered the more active and preferred compounds in lowering blood pressure in hypertensive rats when tested in the procedure given hereinabove.

Pharmaceutical Compositions and Administration

The invention further provides pharmaceutical compositions for administration to living mammals such as humans comprising, as active ingredients, at least one of the compounds according to the invention in association with a pharmaceutical carrier or excipient.

The compounds are presented in a therapeutic form suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidine.

For parenteral administration, the carrier or excipient can be sterile, parenterally acceptable liquid, e.g., water, or a parenterally acceptable oil, e.g., arachis oil, contained in ampules. Exemplary of liquid carriers for oral administration are vegetable oils and water.

In compositions for rectal administration the carrier can comprise a suppository base, e.g., cocoa butter, or a glyceride.

A. Antihypertensive Compositions

Although very small quantities of the active materials of the present invention are effective when minor therapy is involved or in cases of administration to subjects having a relatively low body weight, unit dosages are usually from five milligrams or above and preferably 10, 25, 50, or 100 milligrams or even higher, preferably administered three or four times per day, depending, of course, upon the emergency of the situation, the compound used, and the particular result desired. Twenty-five to 200 milligrams appears optimum per unit dose or usual broader ranges appear to be about 10 to 500 milligrams per unit dose. Daily dosages usually required should range from about 0.3 to about 20 mg/kg/day, preferably 0.3 to 10 mg/kg for the more active compounds. The active ingredients of the invention may be combined with other compatible pharmaceutically active agents. It is only necessary that the active ingredient constitute an effective amount, i.e., such that suitable effective dosage will be obtained consistent with the dosage form employed. Obviously, several unit dosage forms may be administered at about the same time. The exact individual dosages as well as daily dosages will, of course, be determined according to standard medical principles under the direction of a physician.

B. Antiarrhythmia Compositions

Advantageously, the compositions are formulated as dosage units, each unit being adapted to supply a fixed dose of active ingredients. Tablets, coated tablets, capsules, ampules and suppositories are examples of preferred dosage forms according to the invention. It is only necessary that the active ingredient constitute an effective amount, i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests that the oral dosage effective to correct arrhythmias will be about 3 times that of the intravenous dosage.

Based on the animal data, allowing for variation in species and severity of cardiac arrhythmia unit dosages containing an amount of compound equivalent to about 1 to about 100 mg/kg of body weight are contemplated. Based on all of the above considerations, a choice in a range of unit oral dosages for humans of about 10 to about 1000 mg is contemplated, preferably about 10 to 600 mg. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of compositions within the preferred ranges given are as follows:

| Ingredients | Capsules Per Cap. |
|---|---|
| 1. Active ingredient | 10.00 mg |
| 2. Lactose | 146.00 mg |
| 3. Magnesium stearate | 4.000 mg |

Procedure
1. Blend 1, 2 and 3.
2. Mill this blend and blend again.

3. This milled blend is then filled into #1 hard gelatin capsules.

| Tablets (10 mg) | |
|---|---|
| Ingredients | Mg/Tab. |
| 1. Active ingredient | 10.0 mg |
| 2. Corn starch | 20.0 mg |
| *3. Kelacid (Alginic acid) | 20.0 mg |
| *4. Keltose (Algin, sea weed) | 20.0 mg |
| 5. Magnesium stearate | 1.3 mg |

*Available from Kelco Co., Div. of Merck & Co., Chicago, Ill.

| Tablets (50 mg) | |
|---|---|
| Ingredients | Mg/Tab. |
| 1. Active ingredient | 50.0 mg |
| 2. Milo starch | 20.0 mg |
| 3. Corn starch | 38.0 mg |
| 4. Lactose | 90.0 mg |
| 5. Calcium stearate | 2.0 mg |
| | 200.0 mg |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg. |
| 2. pH 4.0 Buffer solution q.s to | 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredient | 5.0 mg. |
| 2. Isotomic Buffer solution 4.0 q.s. to | 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Therapeutic compositions containing an effective amount of one or more compounds of Formula I for controlling cardiac arrhythmias and/or blood pressure are embodiments of this invention.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:
1. A compound selected from the group having the formula:

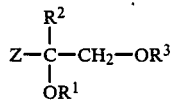

wherein Z is selected from the group consisting of:

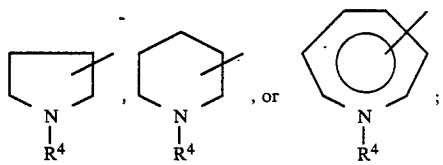

$R^1$ is selected from hydrogen, loweralkyl or carbethoxymethyl;
$R^2$ is selected from hydrogen, loweralkyl, cycloalkyl, phenyl or phenylloweralkyl;
$R^3$ is an aryl group selected from 2,3-dihydroinden-4and 5-yl, phenyl or phenyl substituted by one to three radicals selected from loweralkyl, loweralkoxy, halogen, trifluoromethyl, phenyl, methylenedioxy, nitro, amino, loweralkylamino, diloweralkylamino, and loweracylamino;
$R^4$ is hydrogen or loweralkyl; and
the pharmaceutically acceptable addition salts thereof, and the diastereomers thereof.

2. The compound of claim 1 which is α-phenoxymethyl-2-piperidinemethanol or a pharmaceutically acceptable acid addition salt thereof.

3. The compound of claim 1 which is 2-(1-methoxy-2-phenoxyethyl)piperidine or a pharmaceutically acceptable acid addition salt thereof.

4. The compound of claim 1 which is α-[[1H-2,3-dihydroinden-4-yl)-oxy]methyl]-2-piperidinemethanol or a pharmaceutically acceptable acid addition salt thereof.

5. The compound of claim 1 which is α-[(3,4-dimethylphenoxy)methyl]-2-piperidinemethanol or a pharmaceutically acceptable acid addition salt thereof.

6. The compound of claim 1 which is α-[(2,6-dimethylphenoxy)methyl]-2-piperidinemethanol or a pharmaceutically acceptable acid addition salt thereof.

7. The compound of claim 1 which is α-[(2-ethoxyphenoxy)methyl[-2-piperidinemethanol or a pharmaceutically acceptable acid addition salt thereof.

8. The compound of claim 1 which is α-[(2,4-dimethylphenoxy)methyl]-2-piperidinemethanol or a pharmaceutically acceptable acid addition salt thereof.

9. The compound of claim 1 which is α-[(4-chlorophenoxy)methyl]-2-piperidinemethanol or a pharmaceutically acceptable acid addition salt thereof.

10. The compound of claim 1 which is α-[[(1,1'-biphenyl-4-yl)oxy]methyl]-2-piperidinemethanol or a pharmaceutically acceptable acid addition salt thereof.

11. The compound of claim 1 which is N-[4-[2-hydroxy-2-(2-piperidinyl)ethoxy]phenyl]acetamide or a pharmaceutically acceptable acid addition salt thereof.

12. The compound of claim 1 which is 1-ethyl-α-[[(1H-2,3-dihydroinden-4-yl)oxy]methyl]-2-piperidinemethanol or a pharmaceutically acceptable acid addition salt thereof.

13. The compound of claim 1 which is α-[(2-ethoxyphenoxy)methyl]-1-ethyl-2-piperidinemethanol or a pharmaceutically acceptable acid addition salt thereof.

14. The compound of claim 1 which is α-[(2-chlorophenoxy)methyl]-2-piperidinemethanol or a pharmaceutically acceptable acid addition salt thereof.

15. The compound of claim 1 which is 2-[2-(2-ethoxyphenoxy)-1-(2-piperidinyl)ethoxy]acetic acid ethyl ester or a pharmaceutically acceptable acid addition salt thereof.

16. A method of lowering blood pressure in living animals which comprises administering an effective amount of a compound selected from the group having the formula:

$$\begin{array}{c} R \\ | \\ Z-C-CH_2-OR^3 \\ | \\ OR^1 \end{array}$$

wherein Z is selected from the group consisting of:

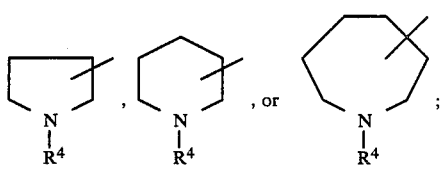

$R^1$ is selected from hydrogen, loweralkyl or carbethoxymethyl;
$R^2$ is selected from hydrogen, loweralkyl, cycloalkyl, phenyl or phenylloweralkyl;
$R^3$ is an aryl group selected from 2,3-dihydroinden-4 and 5-yl, phenyl or phenyl substituted by one to three radicals selected from loweralkyl, loweralkoxy, halogen, trifluoromethyl, phenyl, methylenedioxy, nitro, amino, loweralkylamino, diloweralkylamino, and loweracylamino;
$R^4$ is hydrogen or loweralkyl; and the pharmaceutically acceptable addition salts thereof, and the diastereomers thereof.

17. The method of claim 16 wherein the compound used is α-phenoxymethyl-2-piperidinemethanol or a pharmaceutically acceptable acid addition salt thereof.

18. The method of claim 16 wherein the compound is 2-(1-methoxy-2-phenoxyethyl)piperidine or a pharmaceutically acceptable acid addition salt thereof.

19. The method of claim 16 wherein the compound is α-[[(1H-2,3-dihydroinden-4-yl)-oxy]methyl]-2-piperidinemethanol or a pharmaceutically acceptable acid addition salt thereof.

20. The method of claim 16 wherein the compound is α-[(3,4-dimethylphenoxy)methyl]-2-piperidinemethanol or a pharmaceutically acceptable acid addition salt thereof.

21. The method of claim 16 wherein the compound is α-[(2,6-dimethylphenoxy)methyl]-2-piperidinemethanol or a pharmaceutically acceptable acid addition salt thereof.

22. The method of claim 16 wherein the compound is α-[(2-ethoxyphenoxy)methyl]-2-piperidinemethanol or a pharmaceutically acceptable acid addition salt thereof.

23. The method of claim 16 wherein the compound is α-[(2,4-dimethylphenoxy)methyl]-2-piperidinemethanol or a pharmaceutically acceptable acid addition salt thereof.

24. The method of claim 16 wherein the compound is α-[(4-chlorophenoxy)methyl]-2-piperidinemethanol or a pharmaceutically acceptable acid addition salt thereof.

25. The method of claim 16 wherein the compound is α-[[(1,1'-biphenyl-4-yl)oxy]methyl]-2-piperidinemethanol or a pharmaceutically acceptable acid addition salt thereof.

26. The method of claim 16 wherein the compound is N-[4-[2-hydroxy-2-(2-piperidinyl)ethoxy]phenyl]acetamide or a pharmaceutically acceptable acid addition salt thereof.

27. The method of claim 16 wherein the compound is 1-ethyl-α-[[(1H-2,3-dihydroinden-4-yl)oxy]-methyl]-2-piperidinemethanol or a pharmaceutically acceptable acid addition salt thereof.

28. The method of claim 16 wherein the compound is α-[(2-ethoxyphenoxy)methyl]-1-ethyl-2-piperidinemethanol or a pharmaceutically acceptable acid addition salt thereof.

29. The method of claim 16 wherein the compound is α-[(2-chlorophenoxy)methyl]-2-piperidinemethanol or a pharmaceutically acceptable acid addition salt thereof.

30. The method of claim 16 wherein the compound is 2-[2-(2-ethoxyphenoxy)-1-(2-piperidinyl)ethoxy]acetic acid ethyl ester or a pharmaceutically acceptable acid addition salt thereof.

31. A pharmaceutical composition useful in lowering blood pressure in living animals comprising (a) an effective amount for lowering blood pressure of a compound selected from the group having the formula:

$$\begin{array}{c} R^2 \\ | \\ Z-C-CH_2-OR^3 \\ | \\ OR^1 \end{array}$$

wherein Z is selected from the group consisting of:

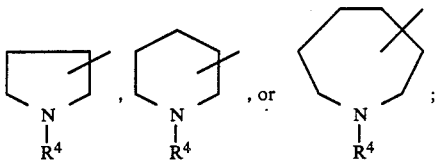

R¹ is selected from hydrogen, loweralkyl or carbethoxymethyl;

R² is selected from hydrogen, loweralkyl, cycloalkyl, phenyl or phenylloweralkyl;

R³ is an aryl group selected from 2,3-dihydroinden-4 and 5-yl, phenyl or phenyl substituted by one to three radicals selected from loweralkyl, loweralkoxy, halogen, trifluoromethyl, phenyl, methylenedioxy, nitro, amino, loweralkylamino, diloweralkylamino, and loweracylamino;

R⁴ is hydrogen or loweralkyl; and the pharmaceutically acceptable addition salts thereof, and the diastereomers thereof.

and (b) a pharmaceutical carrier therefor.

32. The composition of claim 31 wherein the compound is α-phenoxymethyl-2-piperidinemethanol or a pharmaceutically acceptable acid addition salt thereof.

33. The composition of claim 31 wherein the compound is 2-(1-methoxy-2-phenoxyethyl)piperidine or a pharmaceutically acceptable acid addition salt thereof.

34. The composition of claim 31 wherein the compound is α-[[(1H-2,3-dihydroinden-4-yl)oxy]methyl]-2-piperidinemethanol or a pharmaceutically acceptable acid addition salt thereof.

35. The composition of claim 31 wherein the compound is α-[(3,4-dimethylphenoxy)methyl]-2-piperidinemethanol or a pharmaceutically acceptable acid addition salt thereof.

36. The composition of claim 31 wherein the compound is α-[(2,6-dimethylphenoxy)methyl]-2-piperidinemethanol or a pharmaceutically acceptable acid addition salt thereof.

37. The composition of claim 31 wherein the compound is α-[(2-ethoxyphenoxy)methyl]-2-piperidinemethanol or a pharmaceutically acceptable acid addition salt thereof.

38. The composition of claim 31 wherein the compound is α-[(2,4-dimethylphenoxy)methyl]-2-piperidinemethanol or a pharmaceutically acceptable acid addition salt thereof.

39. The composition of claim 31 wherein the compound is α-[(4-chlorophenoxy)methyl]-2-piperidinemethanol or a pharmaceutically acceptable acid addition salt thereof.

40. The composition of claim 31 wherein the compound is α-[[(1,1'-biphenyl-4-yl)oxy]methyl]-2-piperidinemethanol or a pharmaceutically acceptable acid addition salt thereof.

41. The composition of claim 31 wherein the compound is N-[4-[2-hydroxy-2-(2-piperidinyl)ethoxy]phenyl]acetamide or a pharmaceutically acceptable acid addition salt thereof.

42. The composition of claim 31 wherein the compound is 1-ethyl-α-[[(1H-2,3-dihydroinden-4-yl)oxy]methyl]-2-piperidinemethanol or a pharmaceutically acceptable acid addition salt thereof.

43. The composition of claim 31 wherein the compound is α-[(2-ethoxyphenoxy)methyl]-1-ethyl-2-piperidinemethanol or a pharmaceutically acceptable acid addition salt thereof.

44. The composition of claim 31 wherein the compound is α-[(2-chlorophenoxy)methyl]-2-piperidinemethanol or a pharmaceutically acceptable acid addition salt thereof.

45. The composition of claim 31 wherein the compound is 2-[2-(2-ethoxyphenoxy)-1-(2-piperidinyl)ethoxy]acetic acid ethyl ester or a pharmaceutically acceptable acid addition salt thereof.

* * * * *